(12) United States Patent  (10) Patent No.: US 7,731,106 B2
Doner et al.  (45) Date of Patent: Jun. 8, 2010

(54) AIR DRIVEN DELIVERY SYSTEM FOR SPRAYABLE MEDIA

(75) Inventors: August K. Doner, Chelsea, OK (US); G. Thomas Ray, Shreveport, LA (US)

(73) Assignee: Nano Mist International, LLC, Shreveport, LA (US)

( * ) Notice: Subject to any disclaimer, the term of this patent is extended or adjusted under 35 U.S.C. 154(b) by 542 days.

(21) Appl. No.: 11/619,057

(22) Filed: Jan. 2, 2007

(65) Prior Publication Data

US 2007/0164129 A1   Jul. 19, 2007

Related U.S. Application Data

(60) Provisional application No. 60/766,242, filed on Jan. 4, 2006.

(51) Int. Cl.
| B05B 7/30 | (2006.01) |
| B05B 1/00 | (2006.01) |
| F23D 14/60 | (2006.01) |
| F23D 11/46 | (2006.01) |

(52) U.S. Cl. .................. 239/353; 239/345; 239/346; 239/414; 239/600
(58) Field of Classification Search ............ 239/290, 239/296, 345, 346, 353, 390, 427, 319, 413, 239/414, 415, 600; 118/300
See application file for complete search history.

(56) References Cited

U.S. PATENT DOCUMENTS

| 4,100,119 | A |  | 7/1978 | Lerman |  |
| 4,176,205 | A |  | 11/1979 | Molina |  |
| 4,226,740 | A |  | 10/1980 | Worsham et al. |  |
| 4,992,474 | A |  | 2/1991 | Skidmore et al. |  |
| 5,094,400 | A | * | 3/1992 | Ching | 239/341 |
| 5,199,644 | A | * | 4/1993 | Haferkorn | 239/296 |
| 5,319,017 | A |  | 6/1994 | Uenoyama et al. |  |
| 5,435,491 | A | * | 7/1995 | Sakuma | 239/296 |
| 5,662,890 | A |  | 9/1997 | Punto et al. |  |
| 5,710,141 | A |  | 1/1998 | Lin et al. |  |
| 5,725,491 | A |  | 3/1998 | Tipton et al. |  |
| 5,803,367 | A | * | 9/1998 | Heard et al. | 239/296 |
| 5,827,807 | A |  | 10/1998 | Aoshima et al. |  |
| 5,840,278 | A |  | 11/1998 | Coleman |  |
| 5,972,920 | A |  | 10/1999 | Seidel |  |
| 5,980,921 | A |  | 11/1999 | Biedermann et al. |  |
| 6,066,618 | A |  | 5/2000 | Holick |  |
| 6,090,368 | A |  | 7/2000 | Zia et al. |  |
| 6,098,902 | A | * | 8/2000 | Culbertson et al. | 239/290 |
| 6,149,925 | A |  | 11/2000 | Mammone et al. |  |
| 6,299,674 | B1 |  | 10/2001 | Takamura et al. |  |
| 6,337,108 | B1 |  | 1/2002 | Yamaguchi et al. |  |
| 6,395,765 | B1 |  | 5/2002 | Etchegaray |  |

(Continued)

OTHER PUBLICATIONS

International Search Report and Written Opinion, mailed Sep. 22, 2008, from corresponding International Application No. PCT/US2007/060020.

*Primary Examiner*—Dinh Q Nguyen
*Assistant Examiner*—Ryan Reis
(74) *Attorney, Agent, or Firm*—Greenberg Traurig, LLP

(57) ABSTRACT

The present invention relates generally to a gas-compression spray device, wherein the nozzle assembly containing all of the wettable parts is detachable from the body of the spray device.

7 Claims, 23 Drawing Sheets

U.S. PATENT DOCUMENTS

| | | |
|---|---|---|
| 6,458,878 B1 | 10/2002 | Tsuboi et al. |
| 6,589,541 B2 | 7/2003 | Halston et al. |
| 6,612,506 B1 * | 9/2003 | Huang ........................ 239/291 |
| 6,867,229 B2 | 3/2005 | Etchegaray |
| 6,881,782 B2 | 4/2005 | Crater et al. |
| 6,958,142 B2 | 10/2005 | Daniels et al. |
| 6,962,691 B1 | 11/2005 | Lulla et al. |
| 6,962,923 B2 | 11/2005 | Banks et al. |
| 7,029,661 B1 | 4/2006 | DuPuis |
| 7,037,499 B1 | 5/2006 | Glenn et al. |
| 7,105,554 B2 | 9/2006 | Orchard et al. |
| 7,128,897 B2 | 10/2006 | Osbakken et al. |
| 7,350,723 B2 * | 4/2008 | Reedy ........................ 239/332 |
| 2003/0066905 A1 | 4/2003 | Huffman |
| 2003/0071144 A1 | 4/2003 | Naemura |
| 2003/0205631 A1 | 11/2003 | Barron et al. |
| 2004/0022838 A1 | 2/2004 | Holick |
| 2005/0023376 A1 | 2/2005 | Anderson |
| 2005/0242207 A1 | 11/2005 | Tejeda |
| 2007/0164129 A1 | 7/2007 | Doner et al. |

* cited by examiner front view back view

AIR DRIVEN DELIVERY SYSTEM FOR SPRAYABLE MEDIA

This application claims the benefit of U.S. Provisional Application No. 60/766,242, filed Jan. 4, 2006, which application is hereby incorporated by reference.

BACKGROUND OF THE INVENTION

Devices called air brushes enable sprayable media, such as paint and makeup, to be applied without an applicator touching the surface to which the medium is being applied. However, these devices require frequent cleaning, which substantially prolongs the application process. There is a need exists for overcoming drawbacks associated with prior art spray devices.

SUMMARY OF THE INVENTION

The present invention relates generally to devices for spraying sprayable media. In one embodiment, the present invention provides a device with a disposable nozzle, which eliminates the time and effort associated with cleaning the nozzle in conventional devices. In addition, the present invention provides a media container that is disposable. According to one embodiment, the media container of this invention is resealable so that an application process can be interrupted and resumed without affecting the media remaining in the container.

The present invention provides a device for the delivery of facial cosmetics for personal usage and for professional cosmetologist usage. It also serves well as a tool for mortuary cosmeticians. Still further, the system of the present invention may be used for applying tanning products and other personal body-care solutions. In yet another application, the present invention provides a tool for applying paint in many different fields, including the automotive industry, carpentry, model building and arts and crafts generally. Various uses of the present system will be apparent to those in the medical field, where the system may be used to apply topical anesthetics and other sprayable protective and therapeutic compositions. Still further, those specializing in forensic investigations will readily understand the various applications of the present system, such as for the application of fingerprint powder. These and many other features and advantages will be apparent from the disclosure, including the accompanying drawings.

The system of the present system provides an even, controlled and measurable flow of the application medium. In addition, the air gun of this invention can be utilized at any angle, even upside down without affecting the rate or pattern of the dispersal, assuming availability of the media.

In one aspect, the system of this invention provides a disposable spray nozzle. In this manner, when the medium has accumulated in the nozzle to the point where performance deteriorates, the nozzle is simply removed and replaced with a new nozzle. The used nozzle may be simply discarded, thus avoiding the delay associated with frequent nozzle cleaning. Similarly, where it is desired to change to medium (e.g., different color), the entire assembly with the medium cup can be replaced.

The preferred nozzle design has alternate inlet ports, allowing the position of the media inlet to be adjusted for right-handed or left-handed users.

In another aspect, the present invention provides a disposable media cup. The preferred media container of this invention is also designed so that the application process can be suspended for a time and then resumed without affecting the consistency or integrity of the medium. To this end, the container is provided with a vent that can be closed temporarily and reopened when the application procedure is to be resumed. Also, the container port that is removably connected to the nozzle is equipped with a plug, so that the container port can be sealed during the interruption of use.

A cross sectional view of the assembled spray gun is shown in FIG. 1. The gun is shown with the nozzle and spray gun body, without the media container. As described in further detail below, operation of the system begins by placing the desired media in the cup, which may include a mixing ball. Alternately, the user may employ a pre-filled media cup. Once the media is mixed, if necessary, the vent on the top of the cup is opened by twisting the cap over the cup plug until the opening is unobstructed. This will allow media to be pulled through the nozzle without resistance. The source of compressed air or other pressurized gas is connected to the gun.

The trigger is biased by the spring in the closed position, that is, the air stop pin is biased to occlude the silicon tubing. Thus, to operate the system, pressure is applied to the trigger in the downward direction. This lifts the air stop pin off the silicon tubing and allows air to pass through the gun and nozzle. It will be understood now that the trigger also moves forwardly and rearwardly in the handle. This action retracts or advances the needle retractor, which in turn advances or retracts the needle in the nozzle to open or close the media opening in the end of the nozzle. The trigger is spring biased to maintain the needle in the closed position. As is apparent from the drawings, the bi-lobed or "dogbone" shaped end of the needle extending from the rear of the nozzle assembly engagable in the slot in the front end of the retractor of the gun. A twisting motion locks the dogbone in the retractor slot and, at the same time, locks the ears on the nozzle shell inside the nozzle cap of the gun. Simultaneously, the air passage in the nozzle is aligned with the air hole in the front end of the gun.

When thus assembled, a single action (down and back) of the user's thumb or finger exerts control over the flow of air and the release of media from the nozzle. The air passes through the air bore in the front end of the gun up through the side channels in the air plate, through the circumferential openings in the fluid orifice and then out around the nose of the fluid orifice. When the trigger is pressed down, the air flows through this path; when the trigger is released, the air flow is stopped by the air stop pin in the gun. When the trigger is relaxed, that is, in the forwardmost position, the needle is advanced forward, so that the opening through the nose of the fluid orifice is sealed. However, when the trigger is move rearwardly, the needle is retracted, allowing material in the cup to be pulled in by the Venturi effect through the side port on the cup port plate, and through the aligned central openings in the cup port plate, the air plate and the nose of fluid orifice.

The present invention may be used with other types of media containers. For example, the nozzle and gun assembly can be used with a vest containing a battery pack, portable compressor and shoulder bag for holding the media. This allows a person wearing the vest to walk about while dispensing the media, and the media bag can hold a large volume of media. Alternately, the system contemplates the use of a system comprising a set of disposable media cups, such as a set for light, medium and dark makeup.

DETAILED DESCRIPTION OF THE INVENTION

Figure 3:
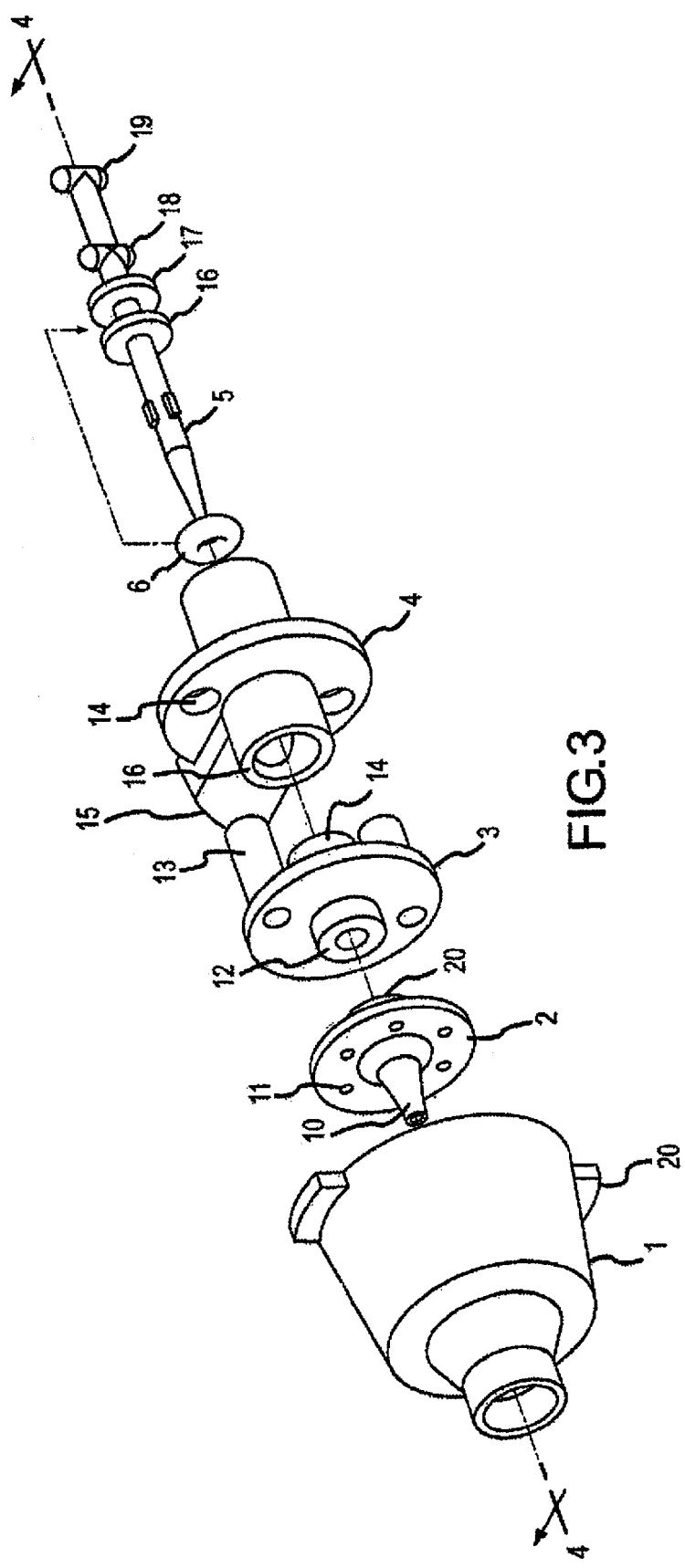
FIG. 3 is an exploded view of the nozzle assembly.
Figure 4:
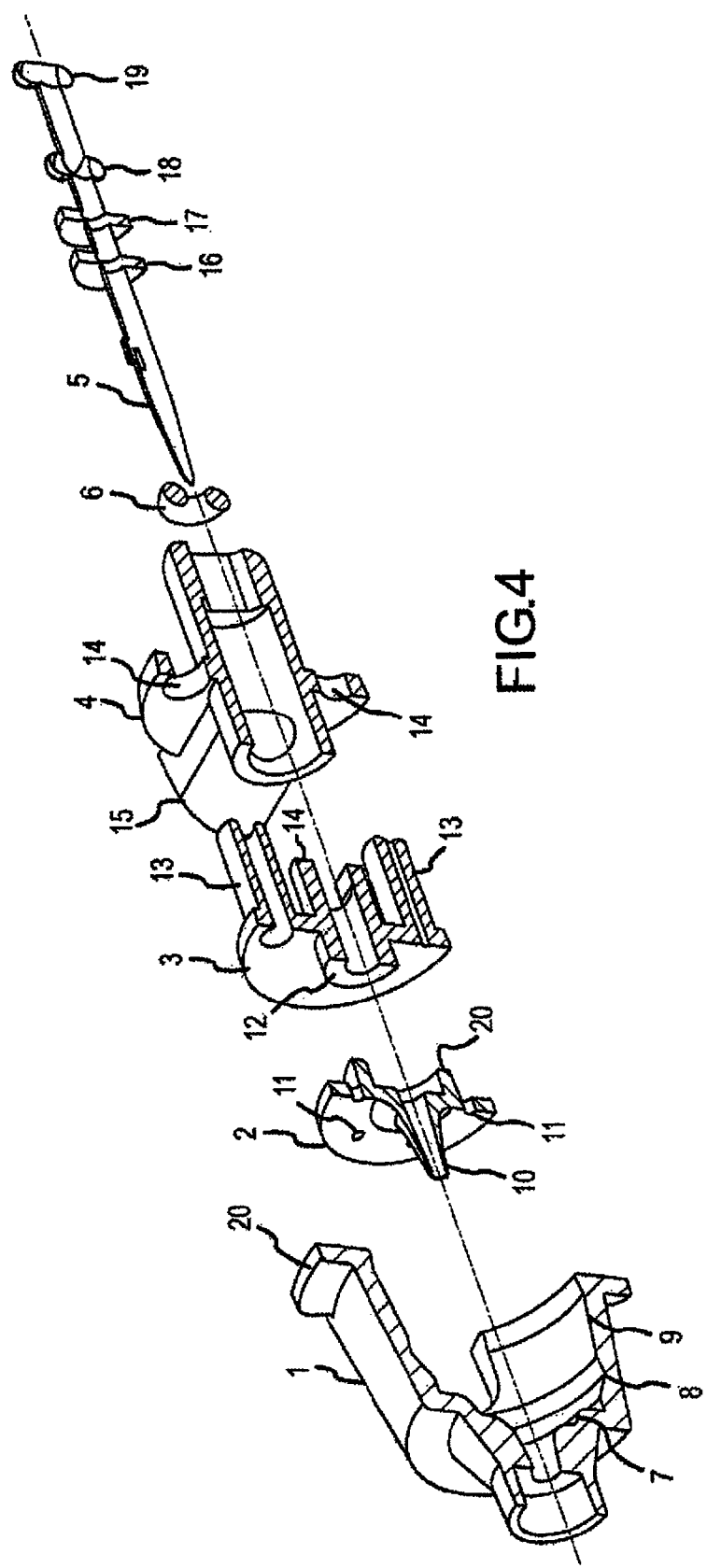
FIG. 4 is a cross sectional exploded view of the nozzle assembly.

The present invention provides a nozzle assembly for a gas-compression spray device comprising an outer shell cap 1, a fluid orifice 2, an air plate 3, a cup port plate 4, and a needle 5 (see FIGS. 1-4)(all dimensions where provided in the Figures are in inches). The outer shell one 1 has an interior and exterior surface and an axial opening for passage of liquid and compressed gas (FIGS. 3, 4). The interior surface preferably has a series of indentations or grooves to accommodate the fluid orifice 2, air plate 3 and cup port plate 4. As such, the first groove 7 would accommodate the outer surface of the fluid orifice 2, the second groove 8 would accommodate the outer surface of the air plate 3, and the third groove 9 would accommodate the cup port plate 4. By accommodate, it is preferred that the outer surface of each part form a seal with the interior of the outer shell 1 to avoid leakage of compressed gas or pressure loss.

The fluid orifice 2 is located within the interior of the cap, the orifice having a forwardly projecting centrally located axially elongated tip 10 with an axial opening for passage of liquid, and one or more circumferential openings 11 for passage of compressed gas. Preferably, the tip 10 will be funnel shaped. The openings 11 can be of any arrangement and number provided that passage of gas along the exterior of the tip 10 results in flow of liquid out of the nozzle tip 10. As shown (see FIG. 3), in one embodiment, there are 6 holes equally spaced in a circumferential arrangement around the base of the tip 10.

The air plate 3 is also located within the interior of the cap 1. The air plate 3 has a centrally located axial opening aligned with the axial opening of the fluid orifice 2 to allow passage of liquid. Preferably, the air plate 3 has raised cylindrically shaped (or other shape) raised surfaces 12, 14 projecting from the front and rear of the air plate, respectively, to provide a sealing surface to prevent leakage of fluid. In addition, the fluid orifice 2 also has a raised surface 20 extending towards the rear of the assembly to fit within or alternatively outside the raised surface 12 to provide an effective sealing surface. Likewise, the rearwardly facing raised surface 14 will fit within a similarly raised surface 16 on the cup port plate 4 to provide a sealing surface between the air plate 3 and cup port plate 4. The air plate 3 also has openings 13 to allow for passage of compressed gas. As shown, these openings may be part of a rearwardly projecting raised cylinder (or other shape). As such, the air port 3 has one or more rearwardly projecting circumferentially located tubes 13 each having an axial opening for passage of compressed gas.

The cup port plate 4 is at least partially located within the interior of the cap 1. Preferably, the outer surface of the cup port plate fits within the $3^{rd}$ groove 9 of the cap 1 and forms a seal with the outer edge of the cap 1. The cup port plate 4 also has a centrally located forwardly projecting tube 16, typically cylindrical in shape, which has an axial opening for passage of liquid. The tube 16 has a side port 15 for accommodating a supply of liquid thereby allowing passage of liquid from the supply into the spray nozzle assembly. The side port 15 is typically substantially perpendicular to the tube 16 and has an opening which is in communication with the axial opening of the tube 16 to allow passage of liquid. The cup port plate 4 also typically has one or more circumferentially located holes 14 corresponding to each of the tubes 13 of the air plate 3.

The nozzle assembly also contains a needle 5 with a forward portion and a rearward portion. The forward portion typically will have a tip which, upon assembly, fits within the axial opening of the elongated tip 10 of the fluid orifice 2. The rearward portion has a means 16, 17 for preventing the rearward flow of liquid through the cup port plate 4, and a means 18, 19 for reversibly engaging a trigger means within the spray device. As shown, the means for reversibly engaging the trigger comprises two lobes (dog bone shape) extending from either side of the shaft of the needle 5. The needle 5 also comprises a gasket 6 which fits between 16 and 17 for providing a seal with the axial opening 16 to further prevent backflow (i.e., rearward flow) of liquid.

According to one embodiment, the interior surface of the outer shell cap 1 comprises three grooves 7, 8, 9. The fluid orifice 2 has a disc-like shape with an outer diameter surface shaped substantially similar to the shape of the first groove 7, where upon assembly, the outer surface will be in sealed communication with the first groove 7. Similarly, the air plate 3 has a disc-like shape with an outer diameter surface shaped substantially similar to the shape of the second groove 8, with the outer surface being in sealed communication with the second groove 8. The cup port plate 15 also has a disc-like shape with an outer diameter surface shape substantially similar to the shape of the third groove 9, with the outer surface being in sealed communication with the third groove 9 and preferably the outer surface is flush with the backside of the outer shell 1.

Figure 1:
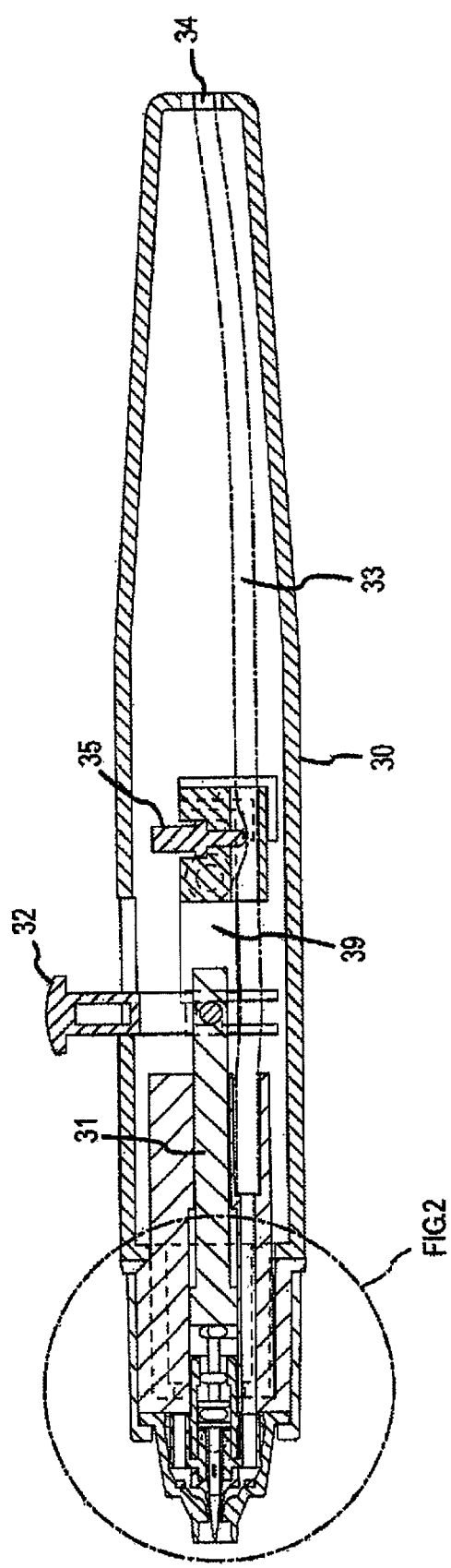
FIG. 1 is a cross sectional view of the device of the present invention.
Figure 2:
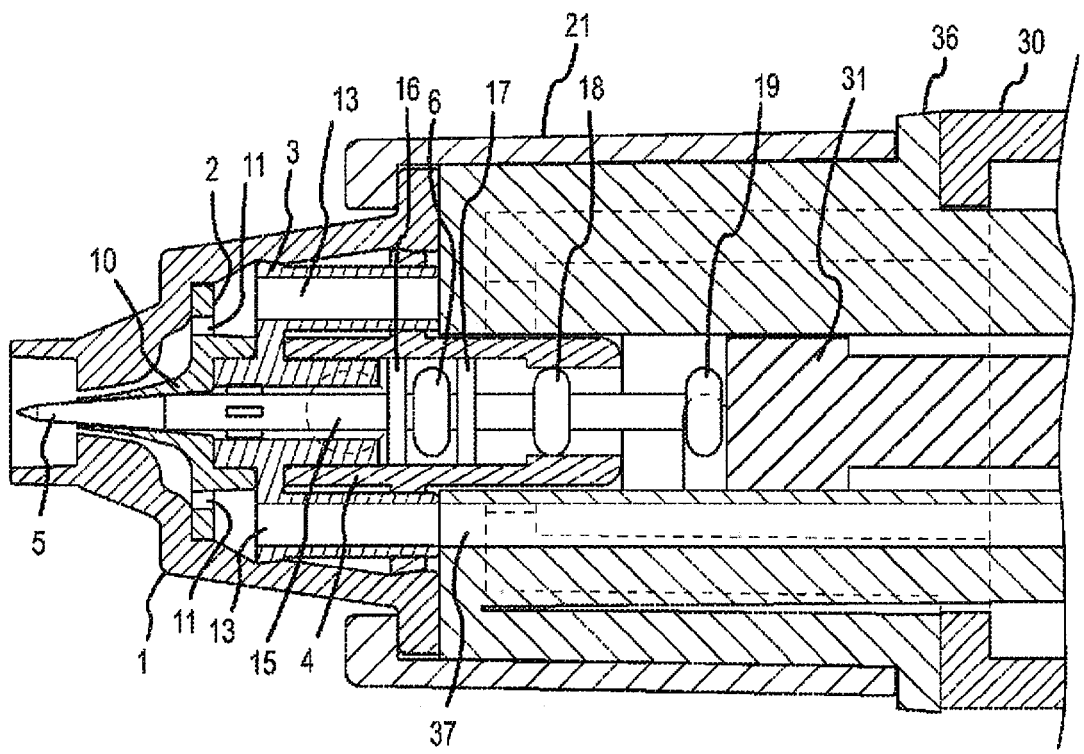
FIG. 2 is a cross sectional view of the nozzle assembly.
Figure 5:
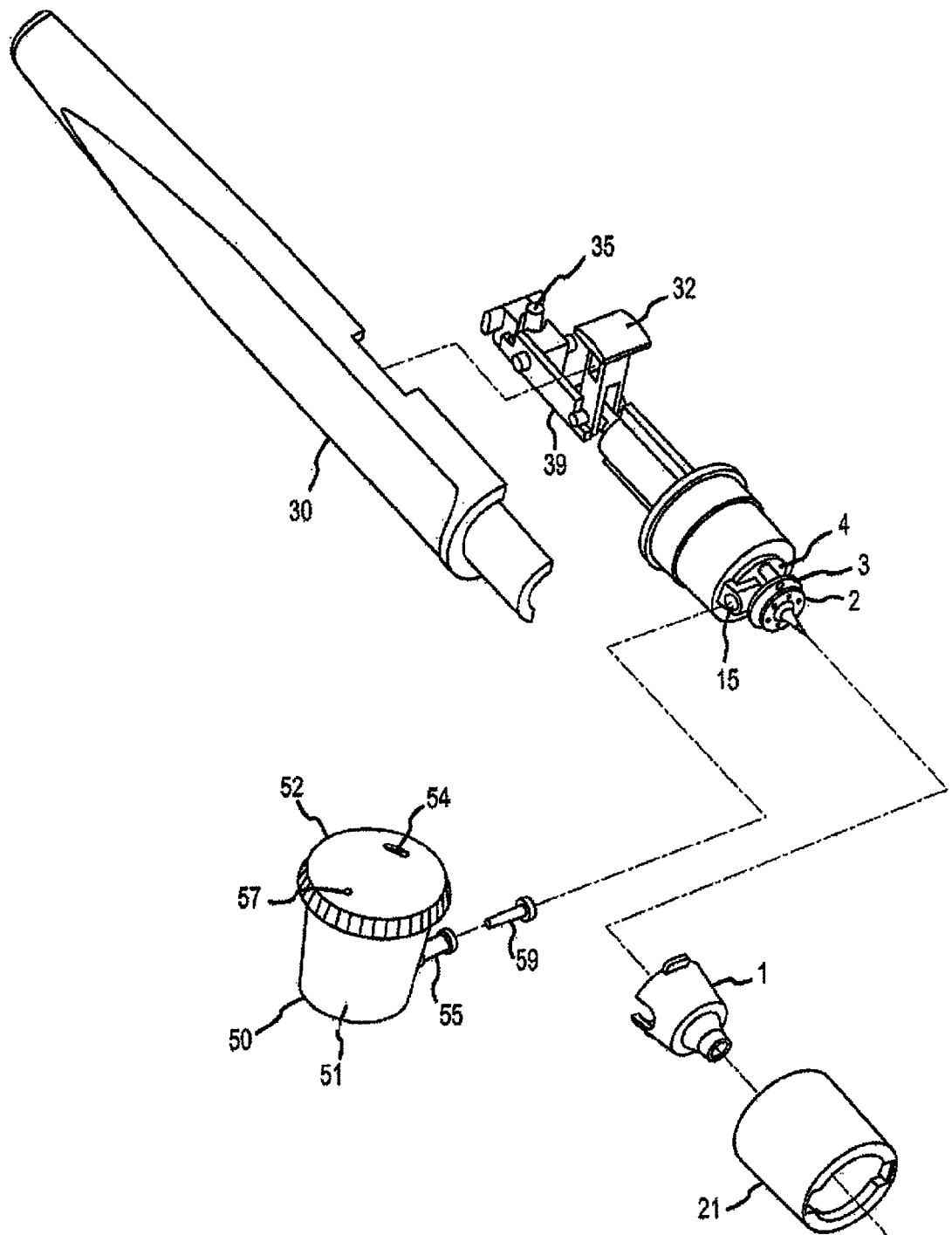
FIG. 5 is an exploded view of the major elements of the device.

The present invention further provide a gas-compression spray device comprising the nozzle assembly 1 and a body 30 (see FIGS. 1 and 5). The nozzle assembly preferably has attached thereto a medium container 50 (FIG. 5) and as such the nozzle assembly contains all of the wettable parts of the spray device reversibly attached to the body. In this embodiment, the nozzle may be easily and conveniently switched in order to change the liquid or the nozzle may be discarded when the nozzle becomes clogged causing, for example, a degradation in the droplet spray. The body 30 preferably has means for controlling the flow of compressed gas and a means for controlling the flow of liquid through the device and into the nozzle assembly. Accordingly, the body 30 may comprise a trigger 32 attached to a needle retractor 31 which in turn is attached to the rearward portion of the needle 5. Preferably, the needle retractor 31 is reversibly attached to the end of the needle 5 via the lobes 19 extending therefrom. In one embodiment, the nozzle assembly is attached to the body via a body cap 36 (see FIG. 2). The body cap 36 has an orifice 38 through which the lobe 19 and the shaft of the needle 5 passes. The needle 5 is attached to the needle extractor 31 by engaging (e.g. through a twisting motion or quarter or half turn) the lobes 19 with the terminal portion of the needle extractor. Upon assembly, a nozzle cover cap 21 may be used to secure the nozzle assembly to the body. The nozzle cover cap 21 may be secured by any means known in the art, e.g., snap on, screw on, etc.

The body 30 will also have a means for delivering compressed gas, such as a flexible air tube 33 and a means for controlling the flow of compressed gas. Typically, the means for controlling the flow of gas will comprise applying pressure to the flexible tube 33 thereby blocking or restricting gas flow. Such means may comprise a valve or air pin 35. The air pin 35 is preferably in a position biased for applying pressure to the tube, using a spring or other means. The body may comprise an actuator bar 39 that is linked to the trigger 21 and the air pin 35, whereby movement of the trigger 32 moves the air pin 35 into an unbiased position releasing pressure on the tube 33 and allowing flow of compressed gas. In one embodiment, the device comprises a "double-independent control means" for controlling flow of compressed gas and liquid, whereby movement of the trigger 32 in an axial direction reversibly controls flow of liquid, and movement of the trigger 32 in a direction perpendicular thereto controls flow of compressed gas.

Figure 6:
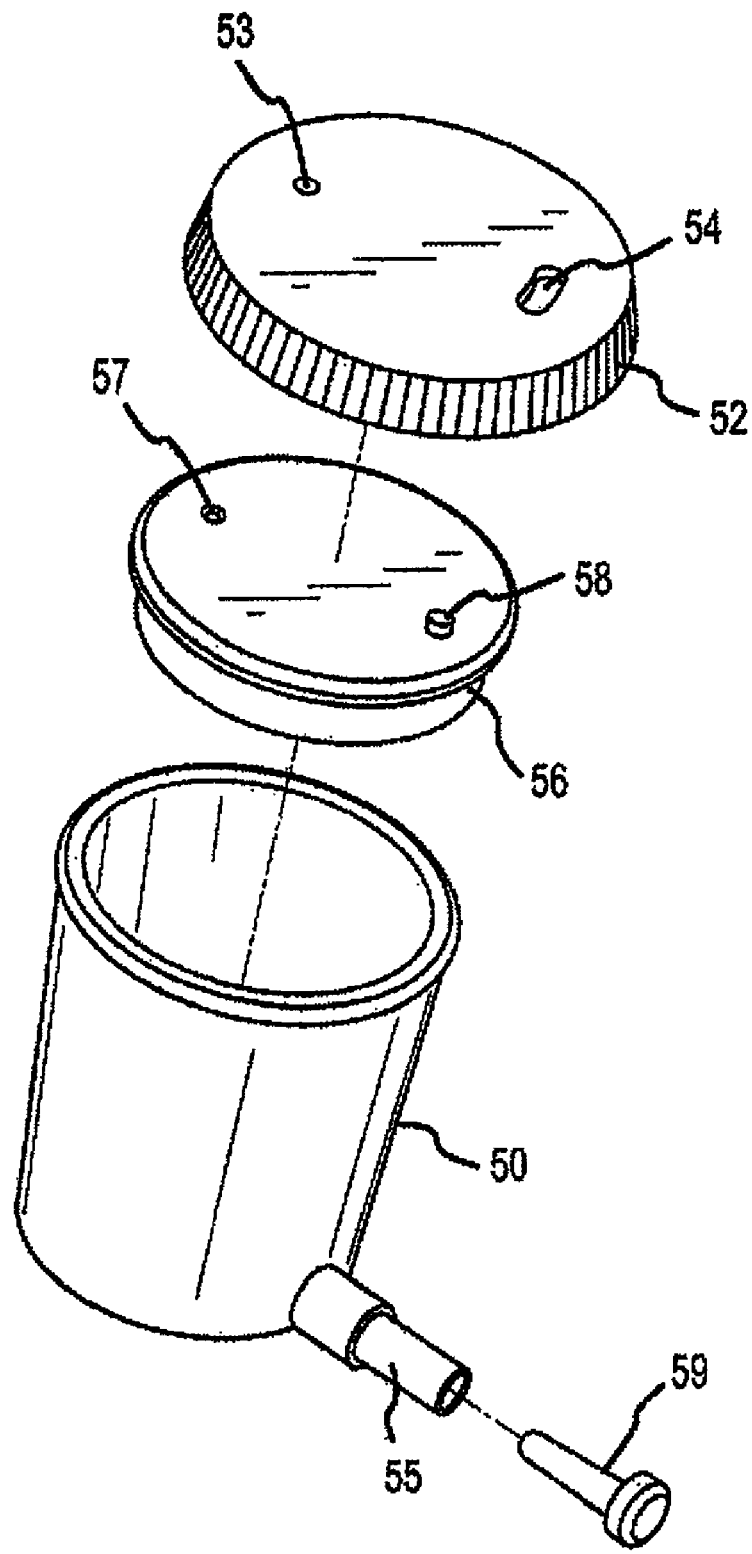
FIG. 6 is an exploded view of the medium container.
Figure 7:
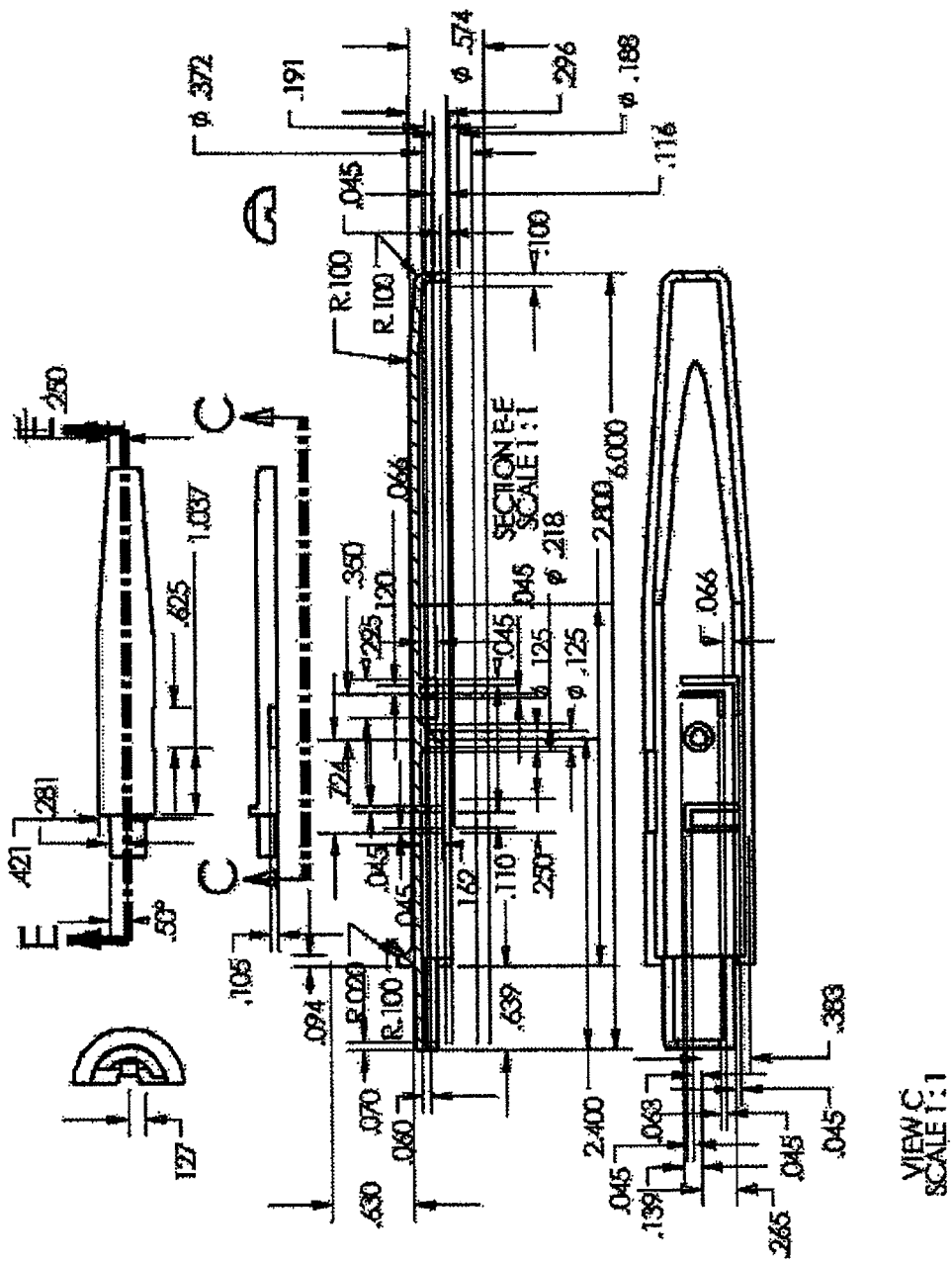
FIG. 7 is a schematic cross section of the body 30.
Figure 8:
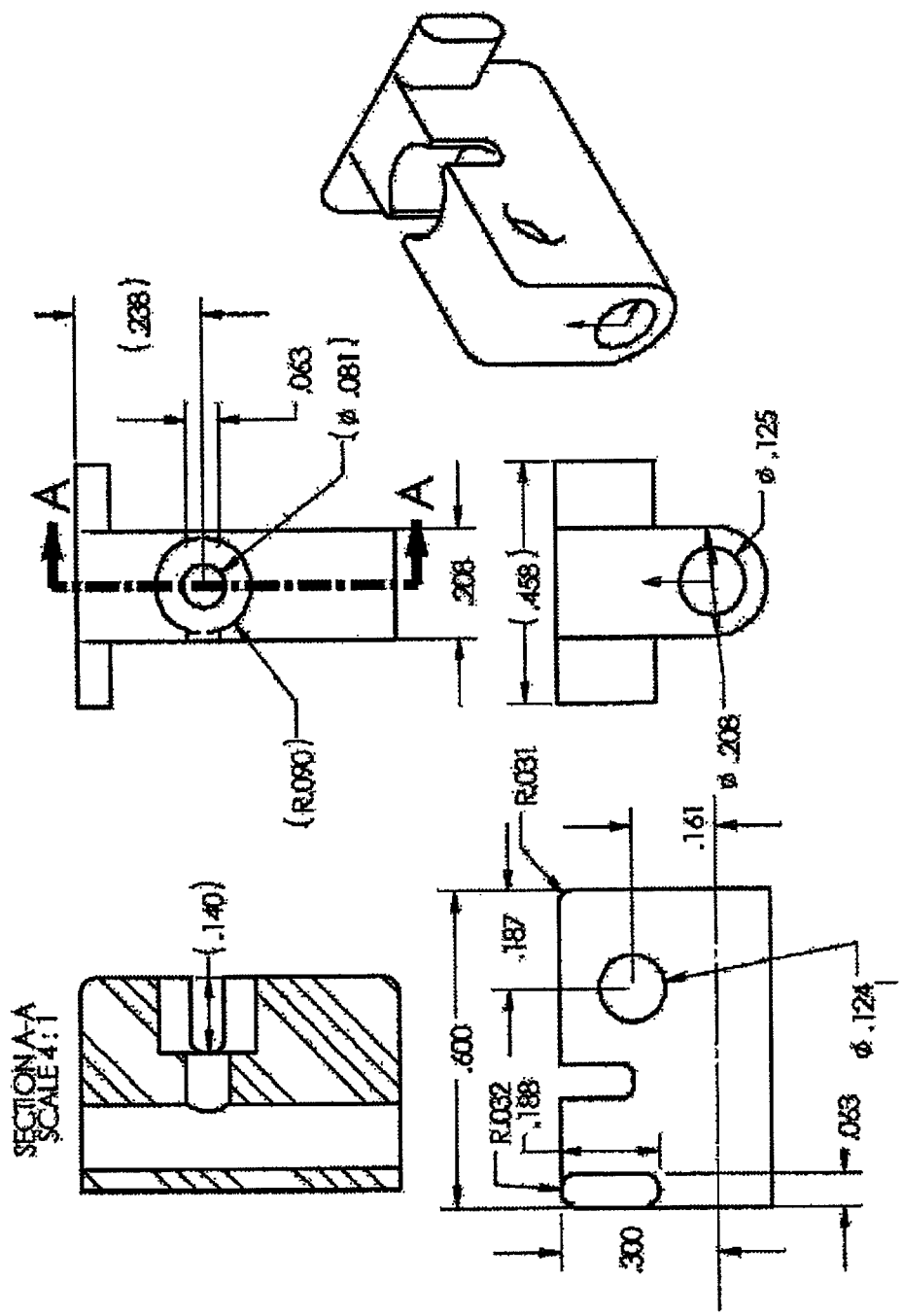
FIG. 8 is a schematic of the air pin holder.
Figure 9:
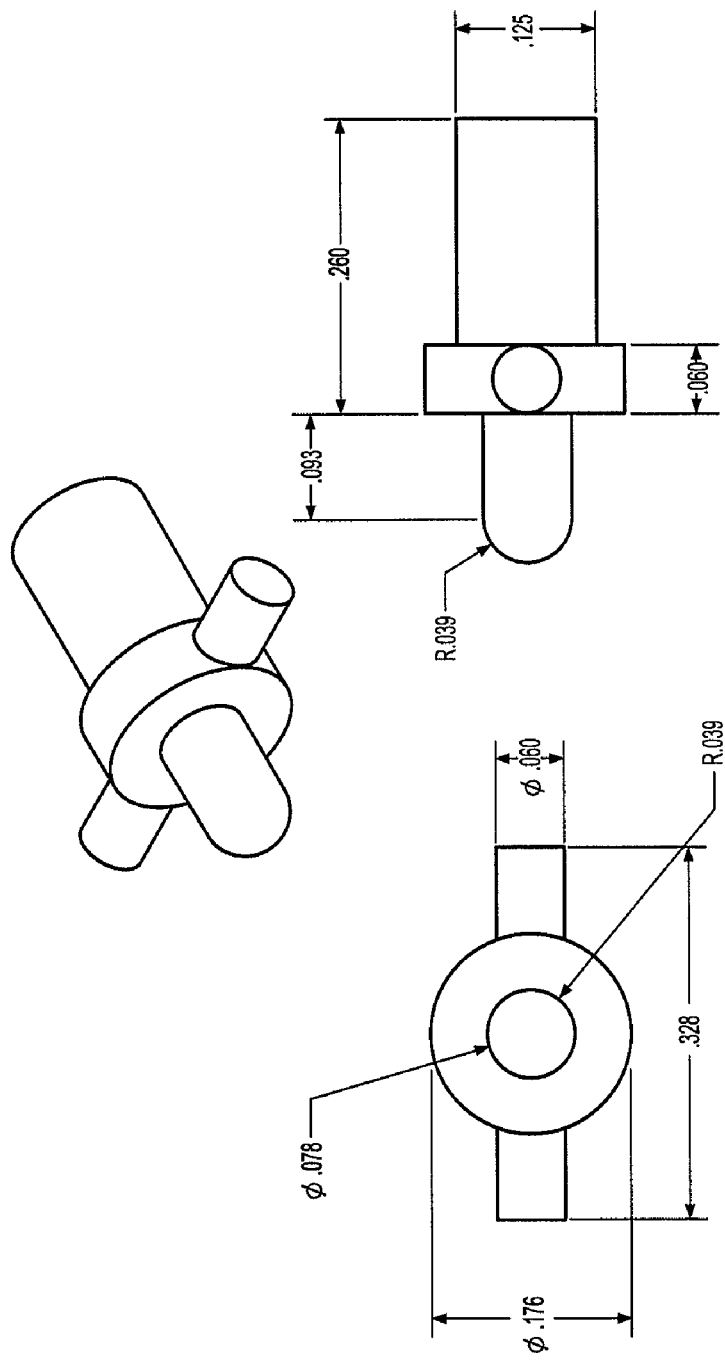
FIG. 9 is a schematic of the air pin 35.
Figure 10:
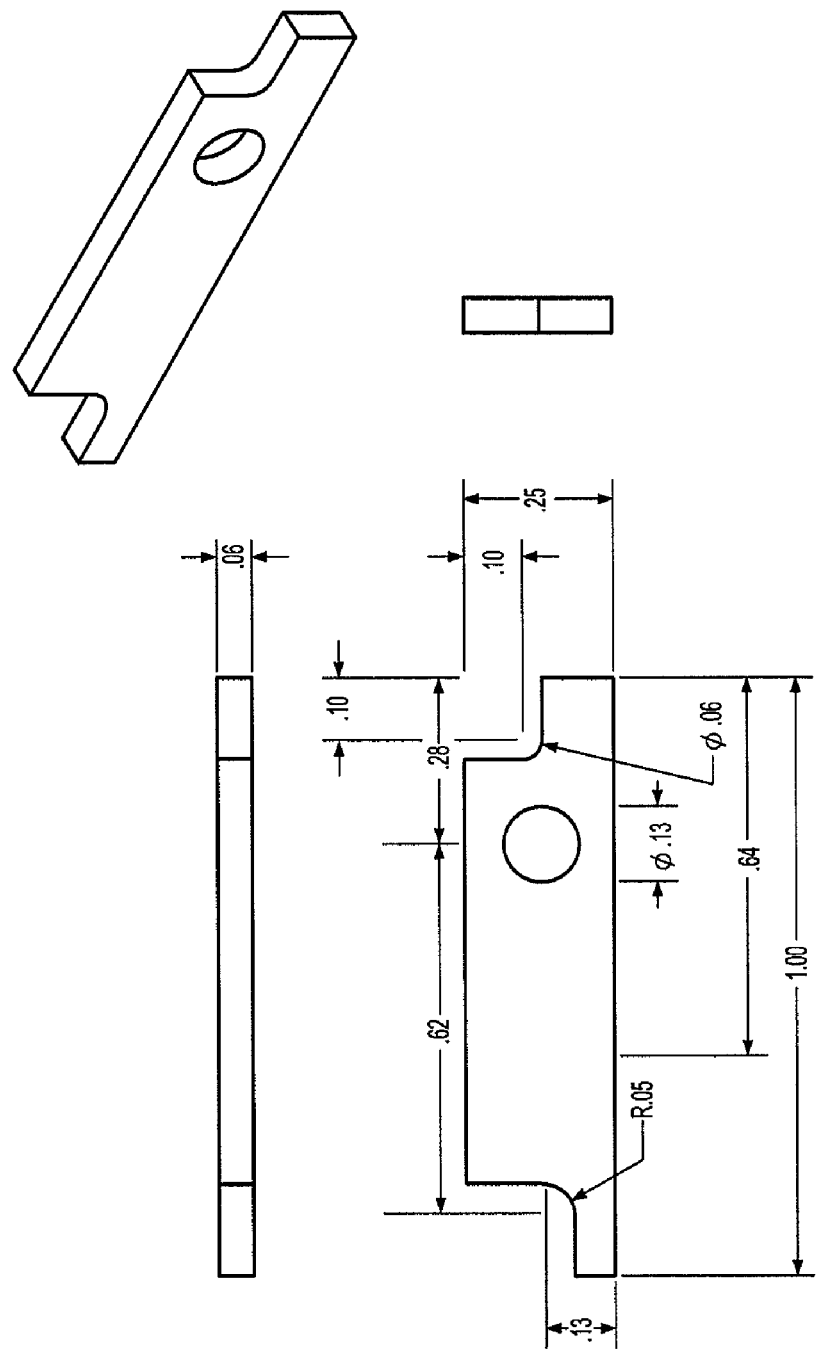
FIG. 10 is a schematic of the actuator bar 39.
Figure 11:
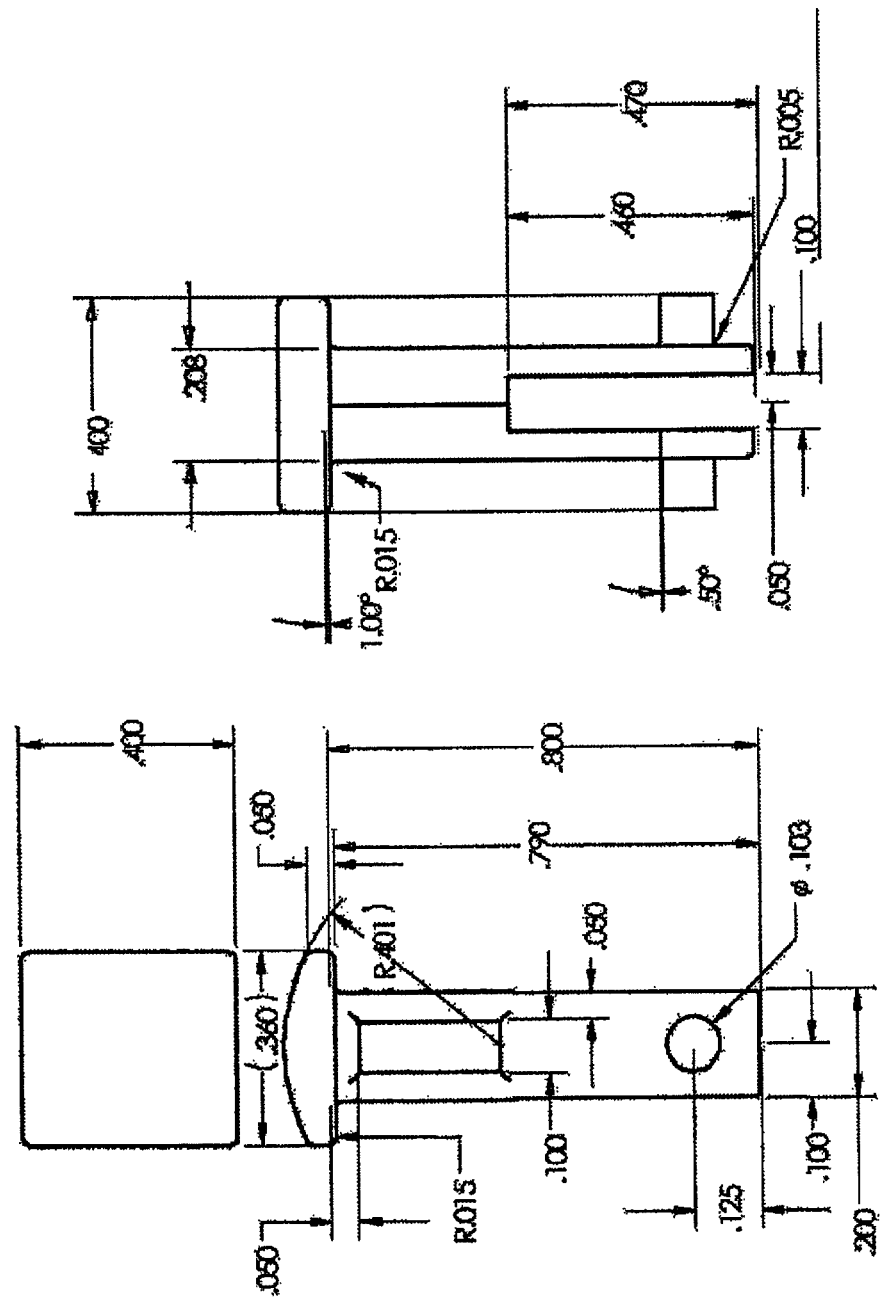
FIG. 11 is a schematic of the trigger 32.
Figure 12:
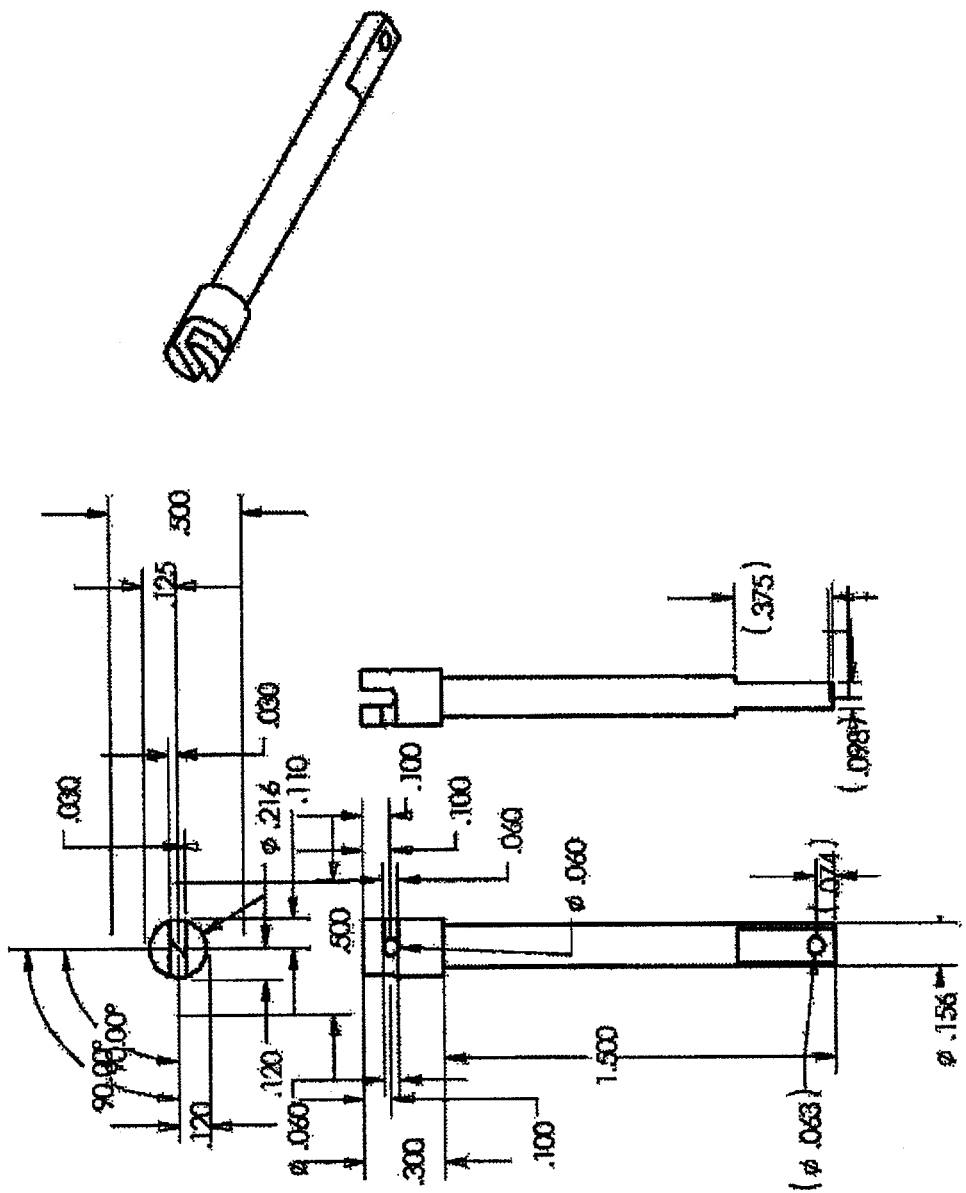
FIG. 12 is a schematic of the needle retractor 31.
Figure 13:
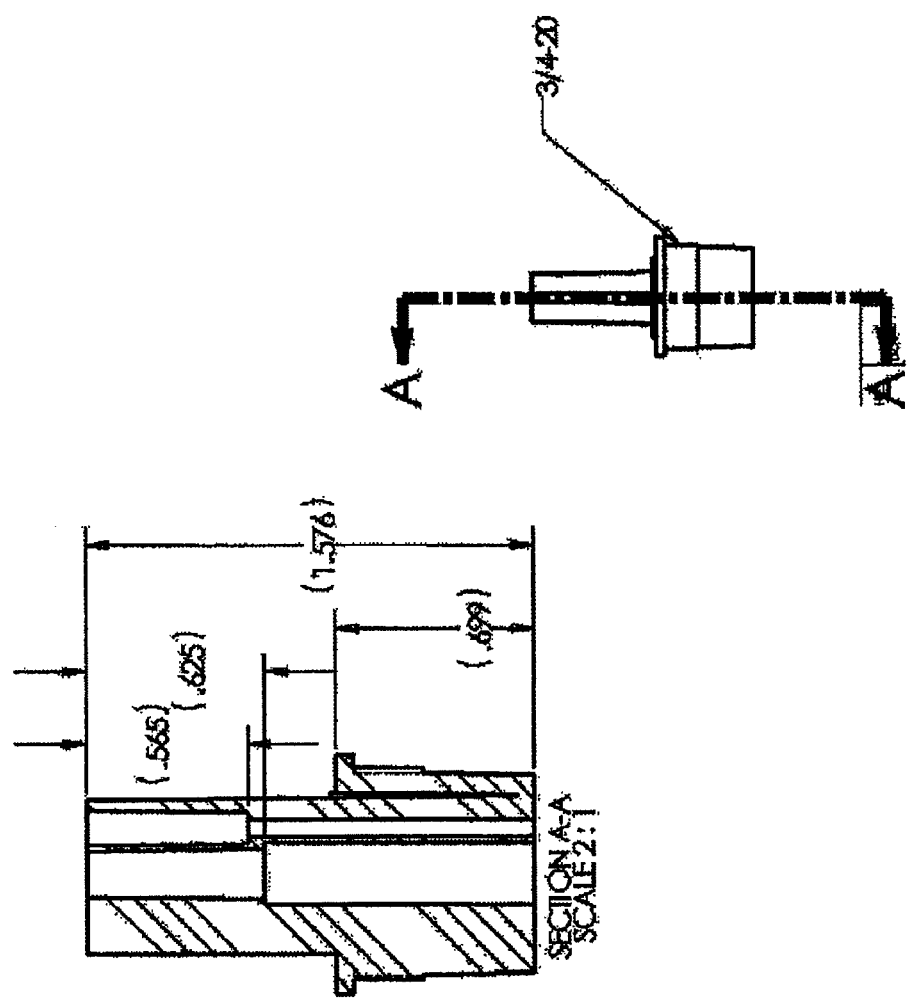
FIG. 13 is a schematic of the body cap 36.
Figure 14A:
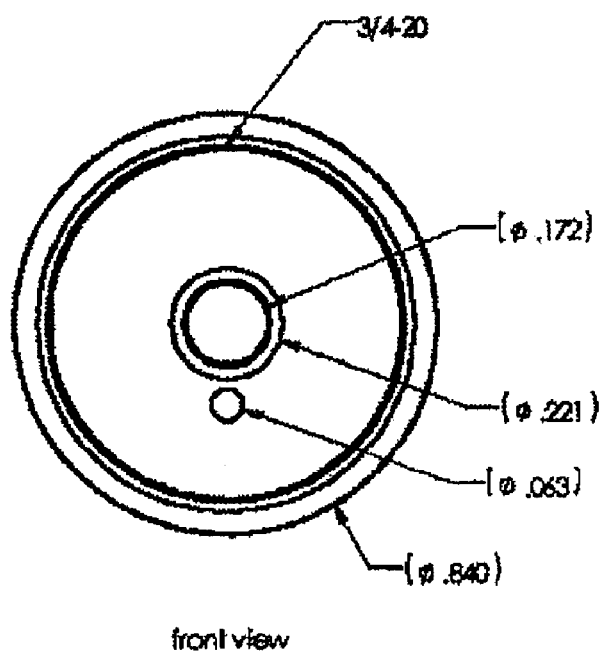
FIGS. 14A and 14B are frontal and rear views, respectively, of the body cap 36.
Figure 14B:
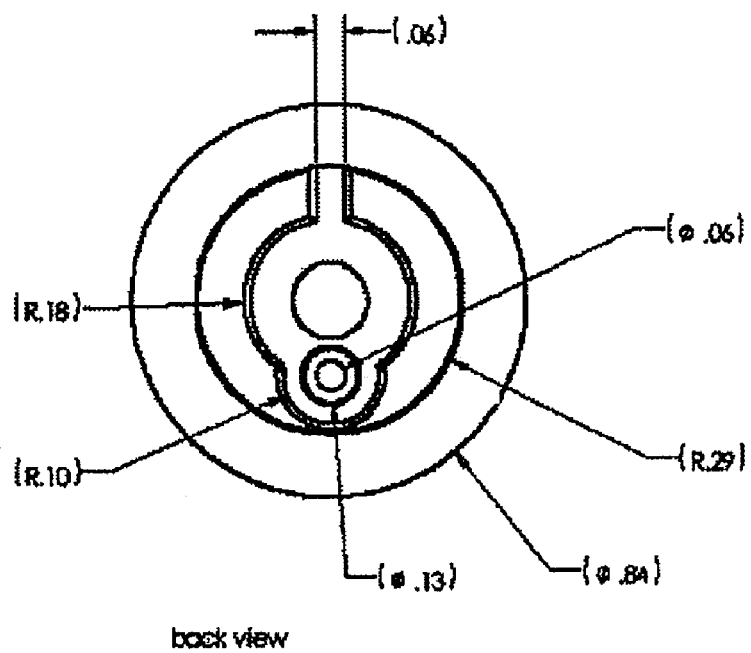
Figure 15:
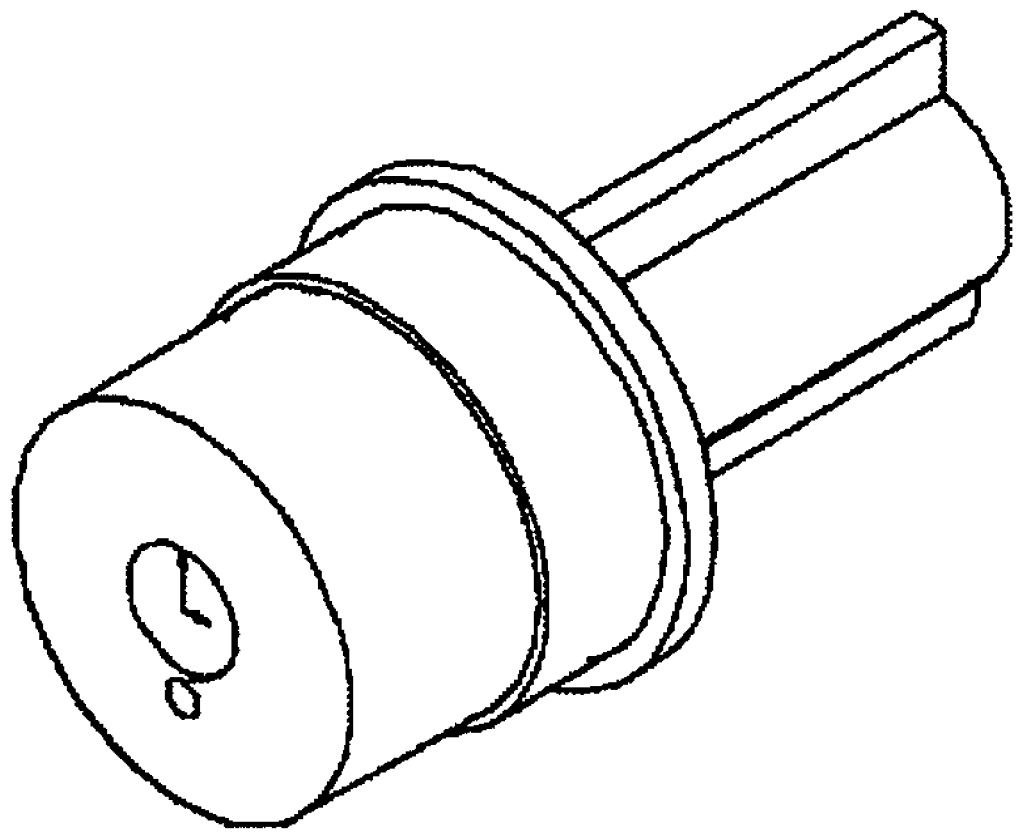
FIG. 15 is an angular view of the body cap 36.
Figure 16:
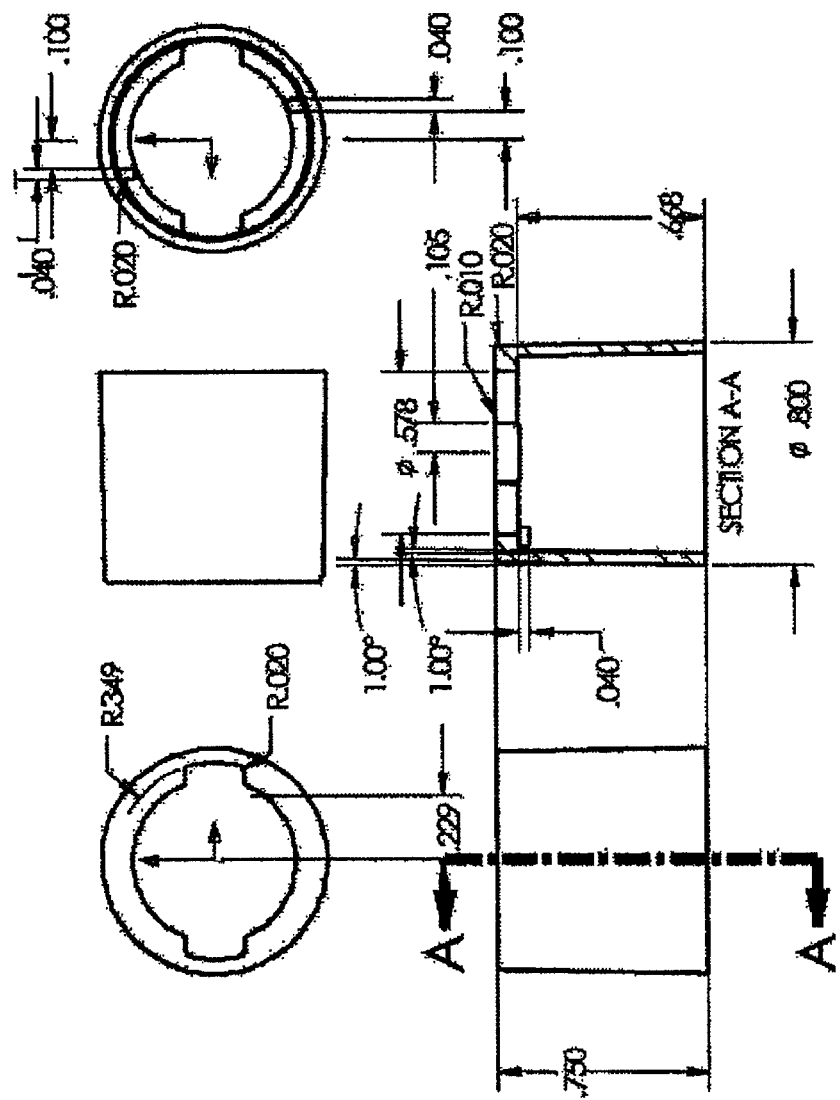
FIG. 16 is a schematic of the nozzle cover cap 21.
Figure 17:
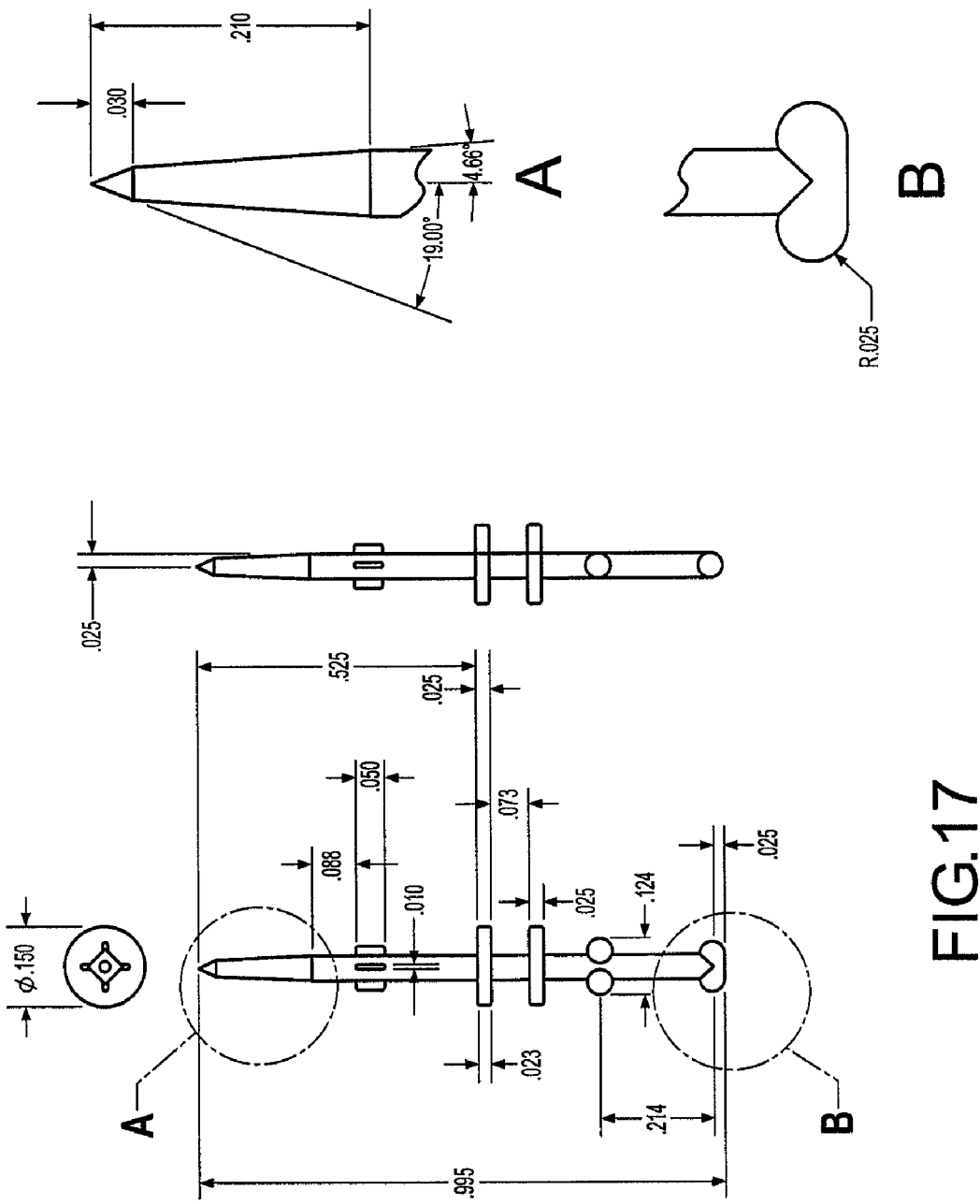
FIG. 17 is a schematic of the needle 5.
Figure 18:
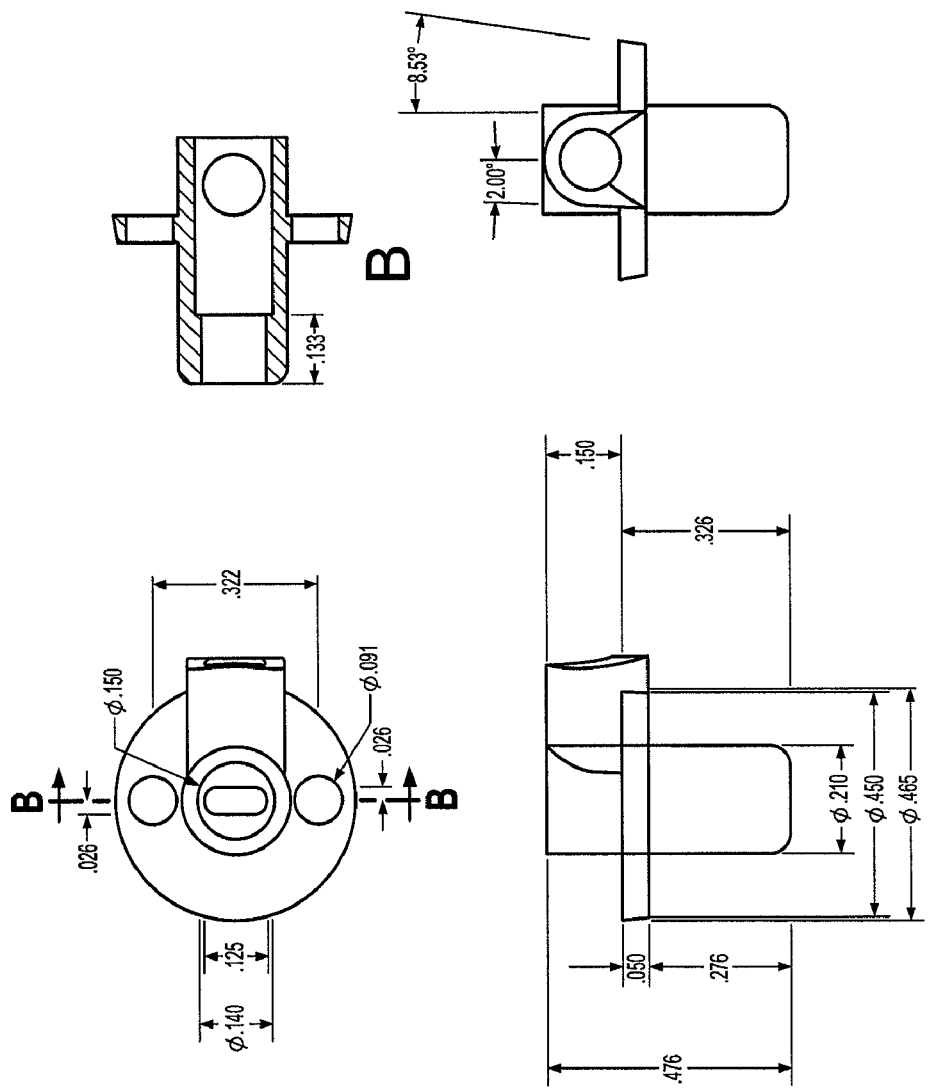
FIG. 18 is a schematic of the cup port plate 4.
Figure 19:
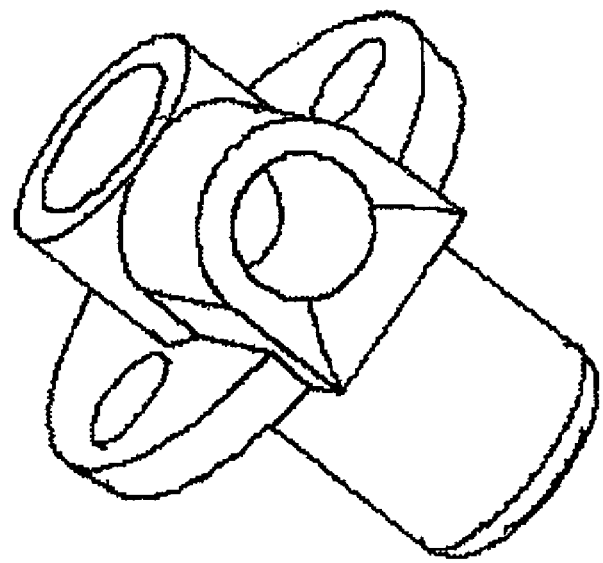
FIGS. 19A and 19B are angular views of the cup port plate 4.
Figure 19B:
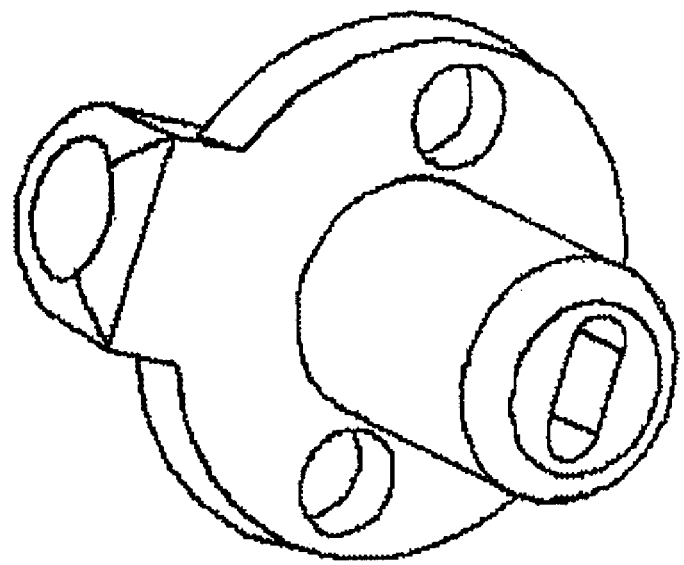
Figure 20:
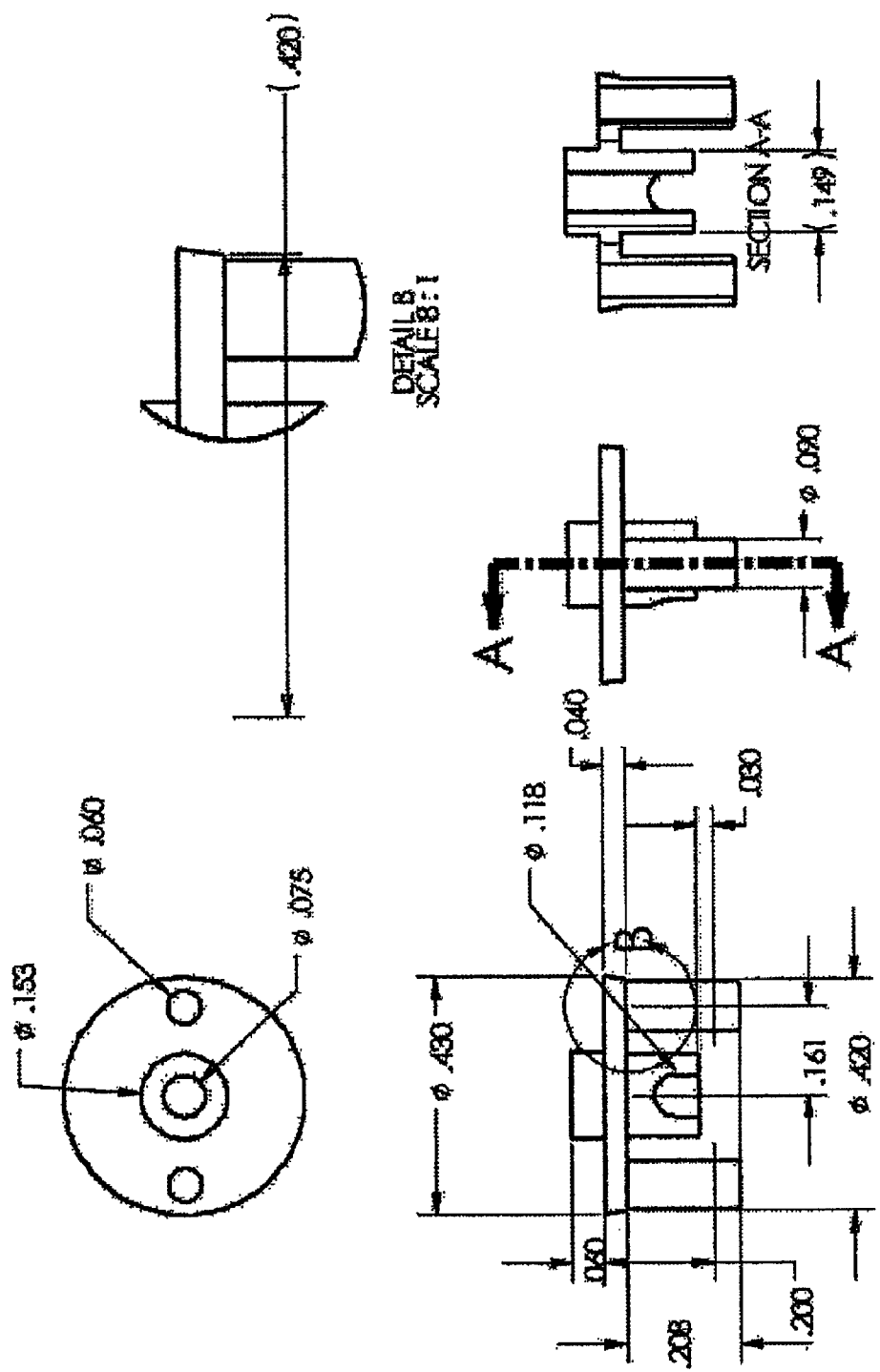
FIG. 20 is a schematic of the air plate 3.
Figure 21A:
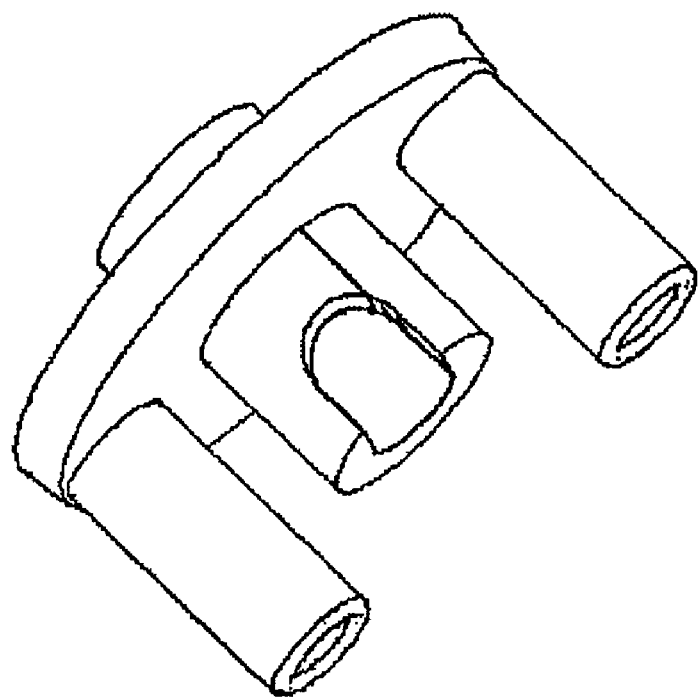
FIGS. 21A and 21B are angular view of the air plate 3.
Figure 21B:
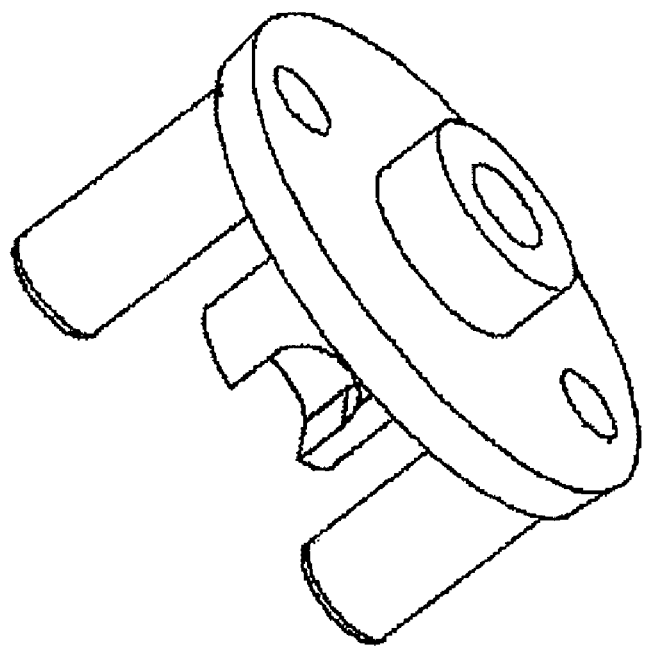
Figure 22:
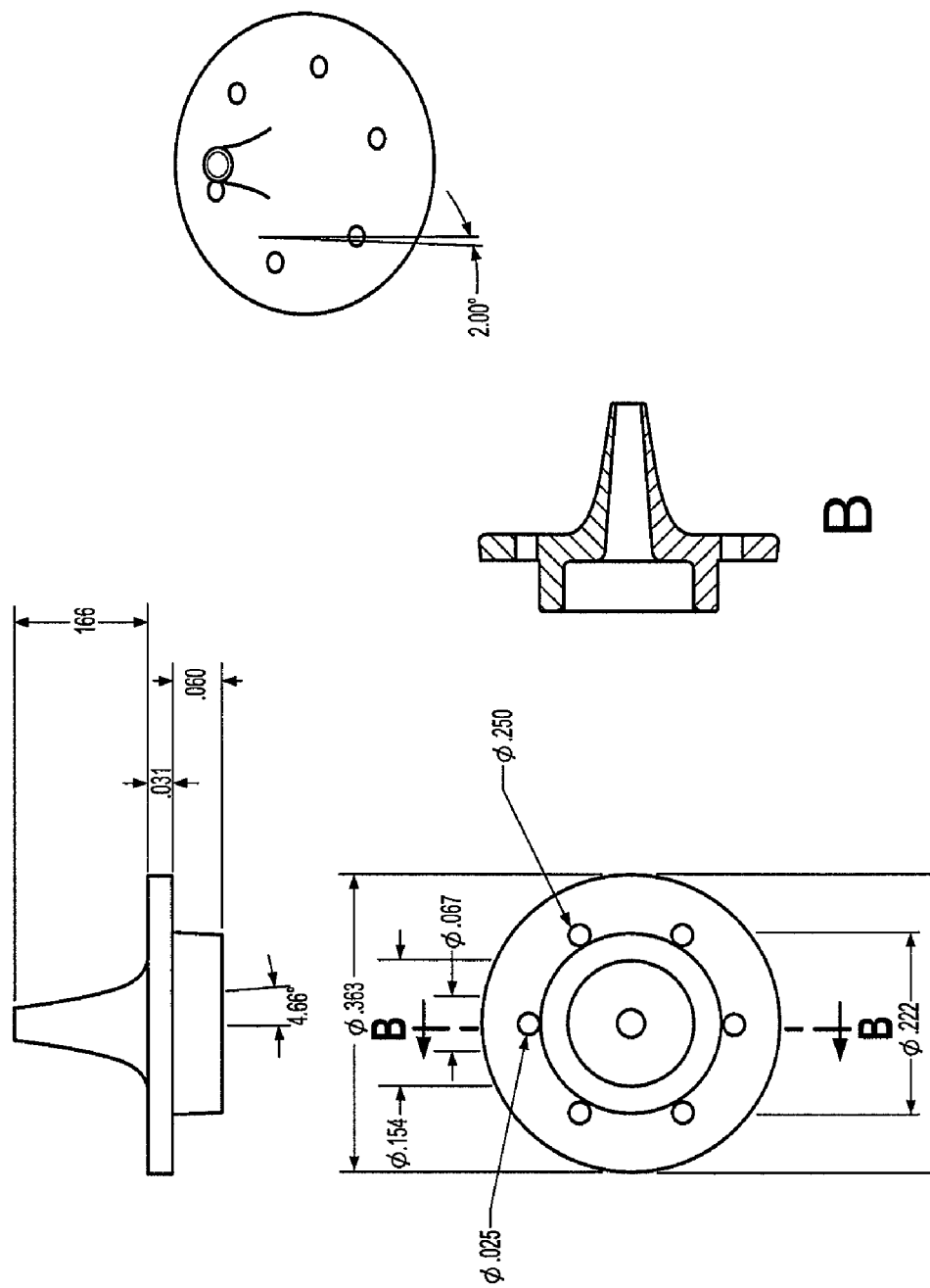
FIG. 22 is a schematic of the fluid orifice 2.
Figure 23:
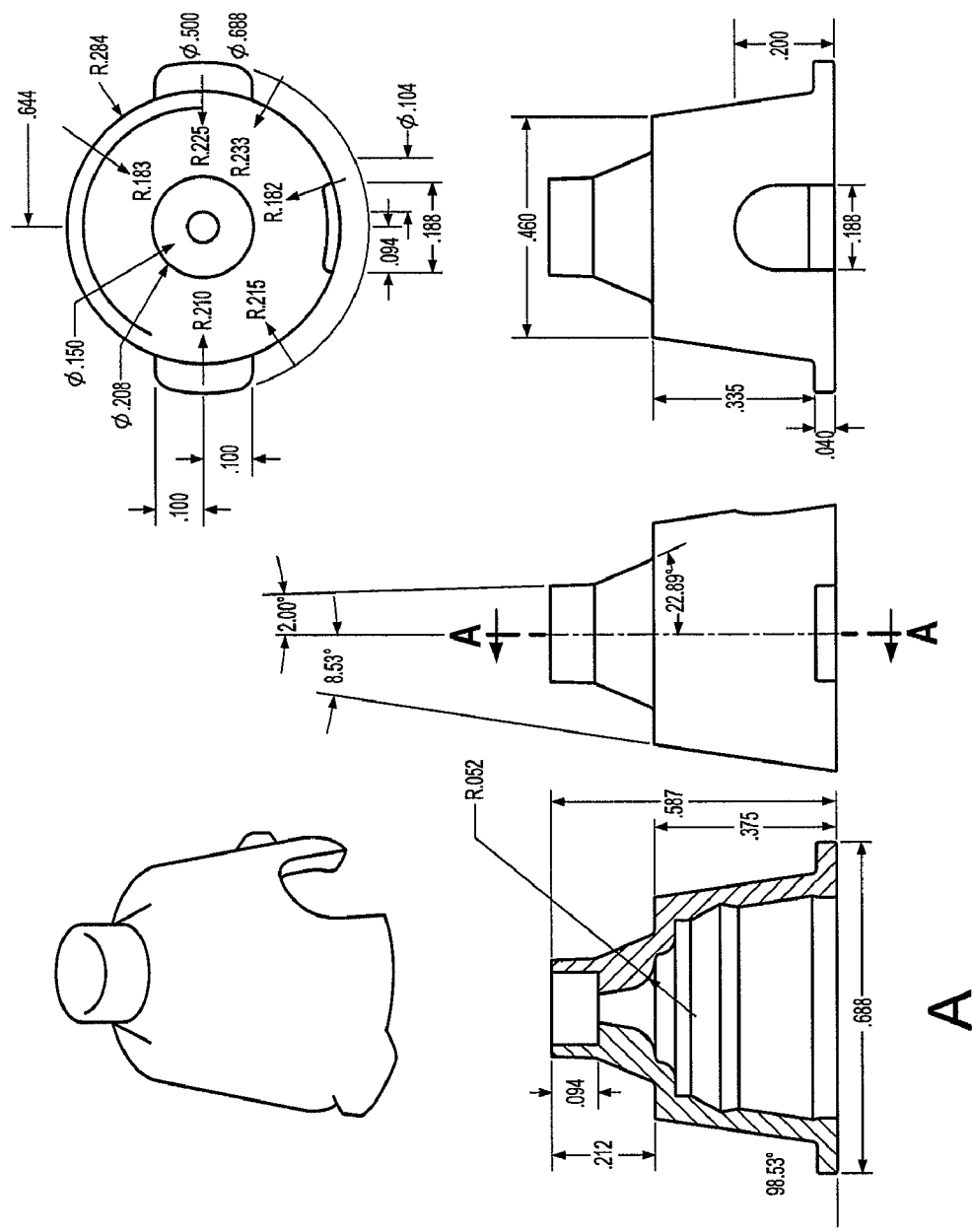
FIG. 23 is a schematic of outer shell cap 1.

As discussed previously, the device will have a source of liquid such as a medium container 51 reversibly engaged with the side port 15 of the cup port plate 4 (see FIGS. 5 and 6). In one embodiment, the medium container 50 will comprise a cup 51 with an open upper portion and an outlet port 55 located in the lower portion for reversible insertion of the medium container 50 into the port 15; a cup plug 56 having an opening 57 and a raised pin 58; and a cup cap 52 having an opening 53 and an aperture slot 54, where the opening 53 is substantially aligned over the opening 57 of the cup plug 56 and the aperture slot 54 being aligned over the raised pin 58. This arrangement allow reversible venting of the cup by twisting or rotating the cup cap 52 thereby allowing alignment of the holes 53 and 57. Rotating in the reverse direction results in blocking of the hole 57 against a solid portion of the cup cap 52. The cup may also have a raised dimple on the underside of the cup cap 52 which reversibly blocks and seals the hole 57 on the cup plug 56. Typically, the cup plug 56 and the cup cap 52 are reversibly attached to the upper portion of the cup 51 to allow the addition of liquid.

Referring to the assembled air brush device (see FIGS. 1 and 5), in operation, downward pressure on the trigger 32 will result in lifting of the air pin 35 allowing compressed gas to flow through the air or gas inlet 34 into the air tube 33, an end of which is attached thereto. Gas will flow through the tube 33 over the length of the body 30 and through an orifice 37 in the body cap 36 (see FIG. 2). Gas will continue to pass through tubes 13 of the air plate, through openings 11 in the fluid orifice, over the tip 10 and out the forward portion of the outer shell. Rearward movement of the trigger 32 will cause retraction of the needle retractor 31 and needle 5 such that the tip of the needle 5 is no longer in contact with the inner wall of the tip 10 of the fluid orifice 2. Through venturi effect, the flow of gas over the outside of the tip 10 will cause flow of liquid from the tip 10.

The present invention may be used to apply any sprayable media or composition. As used herein, "sprayed media" or "sprayable media" refers to any medium—particulate, suspension, or solution—capable of being sprayed onto a surface with an air brush. This includes but is not limited to: (1) cosmetics, such as facial makeup and tanning preparations; (2) paint for various applications, including automotive, carpentry, model building and arts and crafts; (3) medical compositions, such as topical anesthetics, antibiotics and others; and, (4) forensic compositions, such as fingerprint powders and other investigative chemicals.

As used herein, "breathable film" means a film formed on the surface of the skin that does not interfere with perspiration, respiration and other metabolic activities of the skin.

As used herein, "film-formers" means compounds, preferably polymers, that form stable films on a surface when applied. Within the meaning of the present invention, a film is stable if it is resistant to removal by rubbing for an extended period of time. The extended period of time is preferably at least about 24 hours and most preferably from about 1 day to about 5 days.

As used herein, "topical application" means application to a surface such as skin.

As used herein, "topically active" means the composition or medicament for topical application which treats predominately the surface on which it is applied.

As used herein, "percutaneous penetration" or "transdermally available" means that the medicament of the composition is absorbed through skin when applied topically. Typically, although not necessarily, the medicament will then be distributed throughout the body resulting in systemic action as opposed to being only locally active.

As used herein, "permeation enhancer" refers to a component used to enhance the penetration rate of drugs through the skin, preferably by temporarily diminishing the impermeability of the skin. Permeation enhancers have also been called "accelerants" and "sorption promoters." Examples of permeation enhancers include lipophilic solvents, surfactants, menthol, fatty acid esters and polyhydric alcohols.

As used herein, "plasticizer" refers to a component that aids a composition in forming a flexible, adherent film on the skin. Examples of plasticizers include citrate esters, dimethyl isosorbide, castor oil, propylene glycol and polyethylene glycol.

As used herein, "solubilizer" means components that aid in the dissolution or dispersement of the drug in the formulation. Examples of solubilizers include acrylate and methacrylate ester polymers and copolymers, surfactants, polyhydric alcohols, Vitamin E, Vitamin E TPGS and labrasol.

The present disclosure includes a method of applying a topical, medicinal spray composition comprising a drug or combination of drugs as a solution or suspension in a vehicle optionally containing a polymer or combination of polymers which, when sprayed on the surface of the skin, forms a film on the skin. Such compositions are disclosed, for example, in Lulla et al., U.S. Pat. No. 6,962,691, which is incorporated herein in its entirety. However, in the present invention, propellants, such as halogenated hydrocarbons described in Lulla et al. to provide a fine mist, are not needed. The composition may be sprayed on a topical site to form a stable, breathable film on the site, from which film the medicaments act locally on the surface or are transdermally available. Preferably, the composition comprises up to about 7% (w/w) of one or more water-soluble additives (e.g., 0.0001% to about 7%). The drug or combination of drugs so deposited in the matrix of the film-former may remain solubilized or suspended. The exact formulation of the composition will vary depending on the nature of the particular medicament used (for example, the solubility profile) and the release profile desired. The compositions can be dispensed from the air driven delivery system of the present invention dispenser, preferably from the disclosed disposable media cup. The drug from the composition may be released over a period of time or immediately, depending on the selected formulation.

The invention also provides a method of preparing the air driven delivery system containing the pharmaceutical spray composition of the invention comprising mixing the ingredients of the composition and placing the mixed ingredients in the disposable media cup.

The drug can be any medicinal compound in the salt or base form or a combination of compounds which is stable on mixing with the other ingredients of the composition and effective on topical administration. The medicament is preferably a drug which is an antibiotic, an antifungal, an anti-emetic, an anti-anginal, an anti-inflammatory, a steroid, a steroid hormone, a bronchodilator or a drug used to treat osteoporosis. Additional preferred medicaments include drugs used to treat incontinence, antidepressants/anxiolytics, antimigraine agents, agents used in smoking cessation therapy, antidiarrheals, anticholinergics, anticonvulsants, drugs for mood disorders/obsessive compulsive disorder, ACE inhibitors, calcium channel blockers, antihypertensives/diuretics, antiobesity drugs, hormonal peptides and analogues, drugs for benign prostatic hyperplasia/urinary retention and erectile dysfunctions, antiparkinson agents such as dopamine agonists and MAO inhibitors, drugs for sleep disorders, topical analgesics and antidiabetic agents.

One preferred anti-emetic is scopolamine. Preferred anti-anginals include nitroglycerine, clonidine, isosorbide dinitrate, propanolol HCl, timolol maleate, clonazepam and verapamil. Preferred anti-inflammatory drugs include diclofenac sodium, naproxen sodium, ibuprofen, ketoprofen, indomethacin, piroxicam, ketorolac, tromethamine and nimesulide. Preferred steroids include hydrocortisone and esters thereof, dexamethasone, fluocinolone acetonide and betamethasone and salts thereof. Preferred hormonal steroids include estradiol or noethisterone and their pharmaceutically acceptable salts or a combination thereof, testosterone or progesterone. Preferred bronchodilators include salbutamol and salts thereof, bambuterol, salmeterol xinafoate, fluticasone propionate, mometasone furoate, budesonide, beclomethasone dipropionate, sodium cromoglycate and isoprenaline sulphate. Preferred drugs used in case of osteoporosis include alendronic acid, pamidronic acid, etidronic acid and their pharmaceutically acceptable salts. Preferred drugs used to treat incontinence include vasopressin and oxybutynin. Preferred antidepressants/anxiolytics include imipramine, mirtazapine and desipramine. Preferred antimigraine agents include naratriptan, zolmitriptan and sumatriptan. One preferred antidiarrheal is loperamide. One preferred antiulcerant is misoprostol. Preferred anticholinergics include hyoscyamine, atropine and trihexyphenidyl. Preferred anticonvulsants include lorazepam, diazepam and tiagabine. Preferred drugs for antimood disorders/obsessive compulsive disorder include fluoxetine and paroxetine. Preferred ACE inhibitors include lisinopril, trandolapril and captopril. Preferred calcium channel blockers include amlodipine and felodipine. Preferred antihypertensives/diuretics include prazosin and amiloride. Preferred antiobesity drugs include methamphetamine and sibutramine hydrochloride. Preferred hormonal peptides and analogues include GnRH analogues such as nafarelin, leuprolide acetate, insulin and growth hormone and analogues thereof. Preferred drugs for benign prostatic hyperplasia/urinary retention include doxazosin, tamsulosin, terazosin and finasteride. Preferred drugs for erectile dysfunction include alprostadil and sildenafil citrate. Preferred antiparkinson agents include dopamine agonists such as bromocriptine and cabergoline and MAO inhibitors such as selegiline HCl. One preferred agent for sleep disorders is melatonin. Preferred antidiabetic agents include first and second generation sulphonyl ureas such as glimepiride, rosiglitazone, glyburide and glipizide. The chiral forms of all the drugs mentioned above, as well as achiral forms, can be used to make the topical spray composition of the present invention. One preferred hormonal peptide is a peptide analog of human parathyroid hormone or human hypercalcemic factor useful for enhancement of wound healing, and stimulation of hair growth as disclosed by Holick in U.S. Pat. No. 6,066,618.

The film-formers preferably include acrylic polymers or copolymers, including methacrylic polymers and copolymers. Preferred film-formers include a non-ionic copolymer of methyl methacrylate and butyl methacrylate (Plastoid B®), a copolymer of dimethylamine ethyl methacrylate and a neutral methacrylic acid ester (Eudragit E100®), ammonio methacrylate copolymer type B (Eudragit RS®, USP/NF), ammonio methacrylate copolymer type A (Eudragit RL®, USP/NF), methacrylic acid copolymer type A (Eudragit L100®, USP/NF), methacrylic acid copolymer type B (Eudragit S100® USP/NF), polyvinyl acetate, cellulose acetate, polyvinyl alcohol, povidone, povidone vinyl acetate, hydroxypropyl methyl cellulose, hydroxy ethyl cellulose, methyl cellulose and ethyl cellulose.

The breathability of the film is achieved by the absence of any occlusive backing membrane together with the generally hydrophilic properties of the film-forming polymer(s). These polymers can partially dissolve on exposure to moisture (from the skin or air), the dissolution resulting in the formation of a porous film. This porosity can be enhanced by including additional water-soluble additives, such as those detailed below.

Preferred solubilizers may include a copolymer of dimethylamine ethyl methacrylate and a neutral methacrylic acid ester (Eudragit E100®, USP/NF); surfactants, for example, sodium lauryl sulphate; polyhydric alcohols, for example, propylene glycol or polyethylene glycol; vitamin E, vitamin E TPGS (tocopheryl polyethylene glycol 1000 succinate) and labrasol; or any two or more of the above in combination. Preferably, the solubilizer is a copolymer of dimethylamine ethyl methacrylate and a neutral methacrylic acid ester (Eudragit E100®) in combination with, a non-ionic copolymer of methyl methacrylate and butyl methacrylate (Plastoid B®). The solubilizers serve to dissolve the drug in the chosen vehicle. Many of the solubilizers also enhance percutaneous penetration of drug and/or act as humectants.

Preferred plasticizers can include triethyl citrate, dimethyl isosorbide, acetyltributyl citrate, castor oil, propylene glycol, and polyethylene glycol, or any two or more of the above in combination.

The permeation enhancer is preferably a lipophilic solvent, for example, dimethyl sulfoxide, dimethyl formamide or isopropyl myristate; a surfactant, for example, Tweens or sodium lauryl sulfate; menthol; oleic acid, octyl dimethyl para-amino benzoic acid (Padimate 0); mixed esters of capric and caprylic acid; or a polyhydric alcohol, for example, propylene glycol or diethylene glycol monoethyl ether EP (transcutol); or any two or more of the above in combination.

The vehicle can be water or a non-aqueous solvent. Preferred nonaqueous vehicles include acetone, isopropyl alcohol, methylene chloride, methyl-ethyl-ketone, absolute alcohol, ethyl acetate and trichloromonofluoromethane (P11), methyl dimethyl ether or any two or more of the above in combination.

The aqueous or non-aqueous vehicle may additionally comprise (weight/weight of vehicle) up to 20% of one or more humectants. Preferred humectants include polyhydric alcohols and polyvinyl pyrrolidone. Preferred polyhydric alcohols are propylene glycol, butylene glycol, polyethylene glycol, glycerol and sorbitol.

The water-soluble additive is preferably propylene glycol, sodium lauryl sulphate, one or more polaxomers, polyoxyl 35 castor oil, polyoxyl 40 hydrogenated castor oil, cetomacrogol, polyethylene glycol or transcutol, or any two or more of the above in combination.

The instant invention may be used for application of various topical compositions to the skin. For example, one pharmaceutical composition for topical treatment of a fungal infection comprises an antifungal agent, for example, benzylidene thiazolidinediones as disclosed in U.S. Pat. No. 7,105,554 (Orchard et al.). Another sprayable topical pharmaceutical composition useful for treatment of inflammatory and allergic skin diseases, psoriasis, and proliferative skin diseases, comprises 1-phenyl-2-amino-1-ethanol derivatives useful as beta-2 adrenergic stimulants, as disclosed in U.S. Pat. No. 4,992,474 (Skidmore et al.). A further sprayable topical composition for the treatment and protection of the skin of domestic animals which are infested with parasites, or are likely to be infested with them, comprises an insecticidal active substance and a crystallization inhibitor as disclosed in U.S. Pat. No. 6,395,765 (Etchegaray). Another sprayable topical parasiticidal composition for application to the skin of domestic animals which is active against fleas and ticks comprises 1-phenyl:pyrazole insecticide, a crystallization inhibitor, e.g. polyvinyl pyrrolidone, and a solvent mixture, as disclosed in U.S. Pat. No. 6,867,229 (Etchegaray).

A further topical pharmacological composition for the treatment of various skin disorders, including treatment of an inflammatory skin condition, comprises a carrier component, one or more active ingredient components, and a surfactant component. The carrier preferably includes an alcohol in substantially equal volume with isopropyl myristate. The active ingredient component preferably includes a corticosteroid such as clobetasol propionate, an anti-flaking ingredient such as zinc pyrithione, or a combination of the two. The topical spray composition may also include an anti-fungal compound and an surfactant component, preferably includes an alkyl sulfate such as sodium lauryl sulfate, as disclosed in U.S. Pat. No. 5,972,920 (Seidel). A sprayable topical composition for treating acne and related pilosebaceous disorders comprises salicylic acid and pantothenic acid or a pantothenic acid derivative, as disclosed in U.S. Pat. No. 5,710,141 (Lin and Baier).

Another topical, medicinal spray composition for application to the skin comprises a drug or combination of drugs in a carrier which, when sprayed on a surface, forms a film which provides a longer lasting duration of action. The composition comprises at least one medicament, at least one film former and at least one vehicle. The composition may further comprise at least one permeation enhancer, at least one solubilizer, at least one plasticizer, and at least one water soluble additive. A metered dose of the composition can be sprayed on a topical site to form a stable, breathable film, preferably over a fixed surface area. A wide range of medicaments for human and veterinary use may be present that act locally or transdermally, for example, but not limited to an anti-emetic, anti-anginal, antiinflammatory, a steroid, a steroid hormone, a bronchodilator, or a drug used to treat osteoporosis (e.g., alendronate sodium), as disclosed in U.S. Pat. No. 6,962,691 (Lulla et al.).

A further sprayable, topical pharmaceutical composition for treating hyperproliferative skin disorder, such as psoriasis, for enhancing wound healing, for stimulating hair growth, and inhibiting hair growth, comprises one or more of parathyroid hormone (PTH), parathyroid related peptide (PTHrP), or fragment, analog or derivative thereof, and salts thereof, and encapsulated by particular liposomes, as disclosed in U.S. Published Patent Application No. US20040022838A1 (Holick).

One sprayable, topical biodegradable film dressing for human or animal tissue comprises a biodegradable thermoplastic polymer and organic solvent, preferably applied by spraying, as disclosed in U.S. Pat. No. 5,725,491 (Tipton et al.).

Another sprayable topical composition comprises a transcutaneous immunization composition for delivery of an antigen to immune cells without perforation of the skin. This composition, which induces an immune response in an animal or human, comprises an antigen, an adjuvant (preferably an ADP-ribosylating exotoxin), and, optionally, hydrating agents (e.g., liposomes), penetration enhancers, or occlusive dressings, as disclosed in U.S. Pat. No. 7,037,499 (Glenn and Alving).

The instant invention may be used for application of various compositions to the nasal cavity. For example, one nasal spray formulation for female contraception and gynecological disorders comprises gonadotropin-releasing hormone compound and an estrogenic compound dissolved in aqueous medium as disclosed in U.S. Pat. No. 6,958,142 (Daniels et al.).

A longer lasting nasal pharmaceutical composition comprises a water soluble drug admixed with an aqueous bioadhesive cellulosic polymer containing microcrystalline particles, which when sprayed into the nose, drug molecules are retained in contact with the nasal membrane. An exemplary drug composition comprises ketorolac tromethamine, a nonsteroidal aniinflammatory drug, in an aqueous nasal polymeric spray as disclosed in U.S. Pat. No. 6,090,368 (Zia et al.).

Another nasal pharmaceutical composition for treatment of sinusitis comprises one or more anti-infective, antiinflammatory, antimucolytic agents such as cefuroxime, and one or more surfactants effective for retention of the solution in the nasal sinuses, as disclosed in U.S. Pat. No. 7,128,897 (Osbakken et al.). A further nasal pharmaceutical composition for the treatment of recurrent airway obstruction and asthma comprises an endothelin antagonist, as disclosed in U.S. Pat. No. 6,962,923 (Banks et al.). Another nasal pharmaceutical composition for treating common colds comprises, for example, a vitamin component blend consisting of vitamin C, rose hips, acerola and lemon bioflavanoids; a mineral component blend consisting of zinc, potassium, calcium and magnesium; aloe vera and a water-based solvent as disclosed by U.S. Pat. No. 5,840,278 (Coleman).

The air-driven delivery of these compositions offers a significant advance over conventional medicinal topical compositions, since it allows the application of a medicament by a method whereby no physical contact on the area of application is required, except by the film-forming spray itself. The topical films formed by the present compositions will show excellent stability and peelability and can be easily removed from the site of application by washing with water.

The compositions may be prepared by mixing the ingredients, without liquefied propellant, at a temperature of from about 0° C. to about 100° C. The composition so prepared is sprayed from the dispenser onto a topical site, at which site it forms a stable, plastic film or patch.

In general, a composition according to the present invention suitable for use in the air driven delivery system can be prepared as disclosed in Lulla et al., for example, as follows:

1. Dissolve the film former in the chosen vehicle with stirring to form a clear solution;
2. Dissolve or suspend the active ingredient and solubilizer(s) along with the permeation enhancer, together with any water-soluble additives required, in the solution formed in step 1; and
3. Add the plasticizer to the solution and fill the disposable media cup with the mixture.

The following general example illustrates the preparation of a general spray composition according to Lulla et al., which may be used in the disclosed air driven delivery system.

| Ingredients | Percent w/w |
| --- | --- |
| Active ingredient | 0.5-10.0 |
| Plastoid B | 5.6 |
| Eudragit E 100 | 0.6 |
| Propylene glycol | 4.0 |
| Sodium lauryl sulfate | 3.0 |
| Acetone | 20 |
| Isopropyl alcohol | q.s. |
| Vitamin E | 0.2 |
| Transcutol | 2.0 |

Eudragit E 100 is a self-adhesive, hydrophilic matrix system. It also acts as a solubilizer for the drug. Plastoid B is a film-former. When used together, Eudragit E 100 and Plastoid B give better peelability and water washability than when either is used alone. Acetone is a volatile, quick-drying, non-occlusive vehicle which helps to dispense the contents of the spray over a large surface area. Propylene glycol acts as a humectant to prevent the excessive drying of the application site after application of the medicament. It also acts as a plasticizer for the film formed after application. Propylene glycol additionally acts as a solubilizer for the drug and a permeation enhancer. Sodium lauryl sulfate acts as a solubilizer for the drug.

The compositions in the above examples may be discharged from the dispenser as a fine, soft dispersed spray which could be easily controlled to produce a stable thin film of even thickness on a target surface, for example, directly to skin, or a laboratory cover glass. The films may last for at least 24 hours. The concentrations of the film-formers in the composition can be varied as required to obtain a patch which can deliver the drug in a sustained manner for a period of up to 1 to 5 days. The film is easily removable from the application site by water in preparation for reapplication of the film or other treatment.

The instant invention may be used for application of various cosmetic compositions to the skin. For example, a topical cosmetic or pharmaceutical composition for treating skin conditions associated with glutathione depletion in skin cells comprises glutathione-enhancing effective amounts of a glycine compound, a glutamine compound, and a sulfhydryl-containing organic acid, in a cosmetically or pharmaceutically acceptable carrier, as disclosed in U.S. Pat. No. 6,149,925 (Mammone and Gan). Another cosmetic aqueous composition for spray application to hair comprises a polymer with setting and/or conditioning action and copolymer of alkyl acrylate, alkyl methacrylate and unsaturated carboxylic acid to improve spray quality, as disclosed in U.S. Pat. No. 7,029,661 (DuPuis).

A further sprayable cosmetic composition may be used for concealing skin imperfections and accentuating natural features by topical application to form a thin, water-resistant coating that tapers in thickness towards the periphery of the sprayed area, the composition consisting of at least one of a foundation, a shimmer, a bronzer, a glitter, a self-tanning composition, a moisturizer, a toner, a lip color, an eyebrow color, a cheek color and/or an eye color, as disclosed in U.S. Pat. No. 6,589,541 (Halston and Berg).

Another sprayable cosmetic topical composition used for regulating oily and/or shiny appearance of skin comprises niacinamide, pyridoxine, panthenol and/or pantothenic acid and carrier, as disclosed in U.S. Pat. No. 5,980,921 (Biedermann and Deckner).

A further sprayable cosmetic self-tanning composition for artificially tanning skin comprises an aqueous base and dihydroxyacetone, as disclosed in U.S. Pat. No. 5,662,890 (Punto et al.).

Another fingernail polish enamel remover composition comprises acetone, ethylene carbonate, and a monohydric lower alcohol at a specific ratio, has a notable effect for removing enamel painted on nails and has no stimulant, and does not damage nails or skin, as disclosed in U.S. Pat. No. 5,827,807 (Aoshima and Shigeta).

The instant invention may be used for application of various forensic compositions. For example, the device may be used to apply a fingerprint-developing agent which comprises a fixing agent, a diluent and a developer. Useful particularly in forensic investigation, the composition may be applied to a physical surface; and is applicable even to latent fingerprints wet with water, as disclosed in U.S. Pat. No. 6,299,674 (Takamura et al.).

Another sprayable fingerprint development powder which is suitable for developing latent fingerprints comprises a powder carrier, especially a mixture of silica and talc, and a coloring agent, such as a fluorescent dye as disclosed in U.S. Pat. No. 4,176,205 (Molina). The fingerprint powder can be applied by the air driven delivery system thus developing and revealing a bright, sharp fingerprint, which can be photographed or lifted by applying tape or a strippable coating over the print.

A further sprayable fingerprint composition which is responsive to ultraviolet and visible irradiation comprises aluminium powder, carbon black, manganese dioxide, milori blue, mica and gum arabic as disclosed in U.S. Pat. No. 4,226,740 (Worsham and Jenkins).

The instant invention may be used for application of various paint compositions. For example, a sprayable water soluble enamel paint composition may be used which comprises a water soluble polyester resin, and a rosin-ester resin, which improves the water resistance and drying time of the resulting enamel paint, as disclosed in U.S. Pat. No. 4,100,110 (Lerman). Another sprayable paint composition comprises a silyl (meth)acrylate copolymer paint composition which may be used as an antifouling paints for boat hulls or underwater structures as disclosed in U.S. Pat. No. 6,458,878 (Tsuboi et al.).

A further sprayable latex paint composition for application to, e.g., walls, comprises a polymer, a hiding pigment, a thickener, and a polyfluorourethane additive that is the reaction product of isocyanate reactant, fluorochemical compound, and non-fluorinated compound, as disclosed in U.S. Pat. No. 6,881,782 (Crater and Petrin).

Another sprayable powder paint composition comprises specific amount of polyester resin, hydroxyl group content acrylic resin, epoxy resin and urethodione ring content compound, as disclosed in U.S. Pat. No. 6,337,108 (Yamaguchi et al.). A further sprayable reusable water-based paint composition contains water-soluble alkyd or acrylic resin and curing agent with higher solubility parameter, as disclosed in U.S. Pat. No. 5,319,017 (Uenoyama et al.).

The embodiments illustrated and discussed in this specification are intended only to teach those skilled in the art the best way known to the inventors to make and use the invention. Nothing in this specification should be considered as limiting the scope of the present invention. The above-described embodiments of the invention may be modified or varied, and elements added or omitted, without departing from the invention, as appreciated by those skilled in the art in light of the above teachings. It is therefore to be understood that, within the scope of the claims and their equivalents, the invention may be practiced otherwise than as specifically described.

We claim:

1. A gas-compression spray device comprising:
a disposable nozzle assembly, said assembly comprising:
an outer shell cap having an interior and exterior surface and an axial opening for passage of liquid and compressed gas;
a fluid orifice located within the interior of said cap, said orifice having a forwardly projecting centrally located axially elongated tip with an axial opening for passage of liquid, and one or more circumferential openings for passage of compressed gas;
an air plate located within the interior of said cap, said air plate having a centrally located axial opening aligned with the axial opening of the fluid orifice; and one or more rearwardly projecting circumferentially located tubes having an axial opening for passage of compressed gas;
a cup port plate at least partially located within the interior of said cap, said cup port plate having a centrally located forwardly projecting tube having an axial opening for passage of liquid, said tube having an side port perpendicular to said tube and having an opening in communication with said axial opening, said cup port plate having one or more circumferentially located holes corresponding to each of the tubes of the air plate;
a medium container removably attached to the cup port plate; and
a needle with a forward portion and a rearward portion, said forward portion having a tip located within the axial opening of the elongated tip of the fluid orifice, said rearward portion having a means for preventing the rearward flow of liquid through the cup port plate, and a means for reversibly engaging a trigger means within the spray device; and
an air brush body, said body comprising:
a needle retractor having a forward portion and a rearward portion, said forward portion removably attachable to the rearward portion of said needle;
a trigger for controlling the flow of liquid through said device, said trigger being attached to the rearward portion of said needle retractor; and
a means for controlling the flow of gas through said device; and
a double-independent control means for controlling flow of compressed gas and liquid, whereby movement of said trigger in an axial direction reversibly controls flow of liquid, and movement of said trigger in a direction perpendicular thereto controls flow of compressed gas.

2. The device of claim 1 wherein said body further comprises
a means for delivering compressed gas.

3. The device of claim 2 wherein said means for delivering compressed gas comprises a flexible tube; and
said means for controlling the flow of compressed gas comprises a means for applying pressure to said flexible tube whereby gas flow is restricted by said pressure.

4. The device of claim 3 wherein said means for applying pressure comprises an air pin which is in a position biased for applying pressure to said tube.

5. The device of claim 4 wherein said device further comprises an actuator bar linked to said trigger and said air pin, whereby movement of said trigger moves air pin into an unbiased position releasing pressure on said tube and allowing flow of compressed gas.

6. A nozzle assembly for a gas-compression spray device comprising:
an outer shell cap having an interior and exterior surface and an axial opening for passage of liquid and compressed gas;
a fluid orifice located within the interior of said cap, said orifice having a forwardly projecting centrally located axially elongated tip with an axial opening for passage of liquid, and one or more circumferential openings for passage of compressed gas;
an air plate located within the interior of said cap, said air plate having a centrally located axial opening aligned with the axial opening of the fluid orifice; and one or more rearwardly projecting circumferentially located tubes having an axial opening for passage of compressed gas;
a cup port plate at least partially located within the interior of said cap, said cup port plate having a centrally located forwardly projecting tube having an axial opening for passage of liquid, said tube having an side port perpendicular to said tube and having an opening in communication with said axial opening, said cup port plate having one or more circumferentially located holes corresponding to each of the tubes of the air plate; and
a needle with a forward portion and a rearward portion, said forward portion having a tip located within the axial opening of the elongated tip of the fluid orifice, said rearward portion having a means for preventing the rearward flow of liquid through the cup port plate, and a means for reversibly engaging a trigger means within the spray device; and
a medium container attached to the side port of the cup port plate;
said medium container comprises a cup with an open upper portion and an outlet port located in the lower portion for reversible insertion into said port;
a cup plug having an opening and a raised pin; and
a cup cap having an opening and an aperture slot,
said cup plug and cup cap being reversibly attached to the upper portion of said cup;
wherein said cup cap is positioned over said cup plug such that said aperture slot is aligned over said raised pin, whereupon rotation of the cup cap the opening of the cup cap is aligned over the opening of said cup plug.

7. A gas-compression spray device comprising:
a disposable nozzle assembly, said assembly comprising:
an outer shell cap having an interior and exterior surface and an axial opening for passage of liquid and compressed gas;

a fluid orifice located within the interior of said cap, said orifice having a forwardly projecting centrally located axially elongated tip with an axial opening for passage of liquid, and one or more circumferential openings for passage of compressed gas;

an air plate located within the interior of said cap, said air plate having a centrally located axial opening aligned with the axial opening of the fluid orifice; and one or more rearwardly projecting circumferentially located tubes having an axial opening for passage of compressed gas;

a cup port plate at least partially located within the interior of said cap, said cup port plate having a centrally located forwardly projecting tube having an axial opening for passage of liquid, said tube having an side port perpendicular to said tube and having an opening in communication with said axial opening, said cup port plate having one or more circumferentially located holes corresponding to each of the tubes of the air plate; and a needle with a forward portion and a rearward portion, said forward portion having a tip located within the axial opening of the elongated tip of the fluid orifice, said rearward portion having a means for preventing the rearward flow of liquid through the cup port plate, and a means for reversibly engaging a trigger means within the spray device; and an air brush body having a needle retractor having a forward portion and a rearward portion, said forward portion reversibly attached to the rearward portion of said needle;

a trigger for controlling the flow of liquid through said device, said trigger attached to the rearward portion of said needle retractor;

a means for controlling the flow of gas through said device;

a medium container attached to the side port of the cup port plate;

said medium container comprising a cup with an open upper portion and an outlet port for reversible insertion into said port;

a cup plug having an opening and a raised pin; and a cup cap having an opening and an aperture slot, said opening being aligned over said opening of said cup plug and said aperture slot being aligned over said raised pin;

said cup plug and cup cap being reversibly attached to the upper portion of said cup.

\* \* \* \* \*